United States Patent
Singhal et al.

(10) Patent No.: US 9,539,222 B2
(45) Date of Patent: Jan. 10, 2017

(54) METHODS TO INHIBIT INTRACELLULAR GROWTH OF BACTERIA AND TO TREAT BACTERIA-MEDIATED DISEASES

(71) Applicant: Agency for Science, Technology and Research, Singapore (SG)

(72) Inventors: Amit Singhal, Immunos (SG); Gennaro De Libero, Immunos (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 14/426,659

(22) PCT Filed: Sep. 4, 2013

(86) PCT No.: PCT/SG2013/000388
§ 371 (c)(1),
(2) Date: Mar. 6, 2015

(87) PCT Pub. No.: WO2014/039011
PCT Pub. Date: Mar. 13, 2014

(65) Prior Publication Data
US 2015/0209308 A1    Jul. 30, 2015

(30) Foreign Application Priority Data
Sep. 7, 2012 (SG) .................... 201206669-2

(51) Int. Cl.
| | | |
|---|---|---|
| *A61K 31/155* | (2006.01) | |
| *A61K 31/343* | (2006.01) | |
| *A61K 45/06* | (2006.01) | |
| *A61K 31/4422* | (2006.01) | |
| *A61K 31/52* | (2006.01) | |
| *A61K 31/05* | (2006.01) | |
| *A61K 31/7076* | (2006.01) | |
| *A61K 31/277* | (2006.01) | |
| *A61K 31/40* | (2006.01) | |
| *A61K 31/4409* | (2006.01) | |
| *A61K 31/451* | (2006.01) | |
| *A61K 31/675* | (2006.01) | |
| *A61K 31/553* | (2006.01) | |
| *A61K 31/4178* | (2006.01) | |
| *A61K 31/421* | (2006.01) | |

(52) U.S. Cl.
CPC ............ *A61K 31/155* (2013.01); *A61K 31/05* (2013.01); *A61K 31/277* (2013.01); *A61K 31/343* (2013.01); *A61K 31/40* (2013.01); *A61K 31/4178* (2013.01); *A61K 31/421* (2013.01); *A61K 31/4409* (2013.01); *A61K 31/4422* (2013.01); *A61K 31/451* (2013.01); *A61K 31/52* (2013.01); *A61K 31/553* (2013.01); *A61K 31/675* (2013.01); *A61K 31/7076* (2013.01); *A61K 45/06* (2013.01)

(58) Field of Classification Search
None
See application file for complete search history.

(56) References Cited

FOREIGN PATENT DOCUMENTS

| GB | 2465796 A | * | 6/2010 | ........... A61K 31/155 |
|---|---|---|---|---|
| WO | WO-2011/130817 A1 | | 10/2011 | |
| WO | WO-2014/039011 A1 | | 3/2014 | |

OTHER PUBLICATIONS

Database CAPLUS in STN, Acc. No. 2013:385298, Xie et al., Zhongguo Yaofang (2012), 23(28), pp. 2634-2636 (abstract).*
Database CAPLUS in STN, Acc. No. 2010:1043183, Bleskin et al., RU 2396959 C2 (Aug. 20, 2010) (abstract).*
"International Application Serial No. PCT/SG2013/000388, International Search Report mailed Nov. 20, 2013", 7 pgs.
"International Application Serial No. PCT/SG2013/000388, International Preliminary Report on Patentability mailed Jan. 14, 2015", 28 pgs.
"International Application Serial No. PCT/SG2013/000388, Response filed Jul. 7, 2014 to Wirtten Opinion dated Dec. 11, 2013", 23 pgs.
Louw, G. E., et al., "Rifampicin Reduces Susceptibility to Ofloxacin in Rifampicin-resistant *Mycobacterium tuberculosis* through Efflux", published in final edited form as: *Am. J. Respir. Cir. Care Med.*, 184(2), (2011), 269-276
Martins, M., et al., "Inhibitors of $CA_{2+}$ and $K^+$ Transport Enhance Intracellular Killing of M. *tuberculosis* by Non-killing Macrophages", in vivo, 22, (2008), 59-76.
Sanders, J. W., et al., "Azithromycin and Loperamide are Comparable to Levofloxacin and Loperamide for the Treatment of Traveler's Diarrhea in United States Military Personnel in Turkey", *Clinical Infectious Diseases*, 45, (2007), 294-301.
Szabo, C., et al., "Dihydropyridine antagonists and agonists of calcium channels inhibit the induction of nitric oxide synthase by endotoxin in cultured macrophages", *Biochemical and Biophysical Research Communications*, 196(21 (1993), 825-830.
Zmijewski, J. W., et al., "Mitochondrial Respiratory Complex I Regulates Neutrophil Activation and Severity of Lung Injury", *Am. J. Respir. Crit. Care Med.*, 178, (2008), 168-179.

* cited by examiner

*Primary Examiner* — Brian J Davis
(74) *Attorney, Agent, or Firm* — Schwegman Lundberg & Woessner, P.A.

(57) ABSTRACT

Disclosed is a method of preventing, treating or inhibiting bacterial infections. The method comprises administering at least one of the compounds disclosed herein. Also disclosed are methods of increasing acidity of bacterial phagosomes to inhibit bacterial growth, methods of increasing mitochondrial reactive oxygen species (mROS) generation to inhibit bacterial growth in a cell, pharmaceutical compositions and uses thereof.

15 Claims, 14 Drawing Sheets

(A)

(B)

(C)

(A)

(B)

B)

(A)

(B)

(A)

(B)

(C)

A

B

C

A.

B.

A.

B.

METHODS TO INHIBIT INTRACELLULAR GROWTH OF BACTERIA AND TO TREAT BACTERIA-MEDIATED DISEASES

PRIORITY CLAIM TO RELATED APPLICATIONS

This application is a U.S. national stage application filed under 35 U.S.C. §371 from International Application Serial No. PCT/SG2013/000388, which was filed Sep. 4, 2013, and published as WO 2014/039011 on Mar. 13, 2014, and which claims priority to Singapore Application No. 201206669-2, filed Sep. 7, 2012, which applications and publication are incorporated by reference as if reproduced herein and made a part hereof in their entirety, and the benefit of priority of each of which is claimed herein.

FIELD OF THE INVENTION

The present invention generally relates to the field of immunology. In particular, the present invention relates to compounds that enhance an immune response. Also disclosed are compounds and methods for treating bacterial infections.

BACKGROUND OF THE INVENTION

Antibiotics or antibacterial agents are agents that are used to inhibit the growth of or kill bacteria. As commonly known, bacteria can develop resistance to antibiotics or antibacterial agents. Resistance of a bacterium to an antibiotic can range from substantially greater tolerance or reduced susceptibility to completely unaffected by the antibiotics. When a bacterium cannot be controlled or killed by antibiotics or antibacterial agents, the bacteria is able to survive, multiply and cause disease or damages to the hosts despite being in the presence of the antibiotic when such scenario occurs, the bacteria is considered resistant to drug (i.e. drug resistant bacteria). Due to the increased reliance on antibiotics to treat common diseases, antibiotic resistant bacteria are rapidly on the rise. Such antibiotic resistant bacteria have become a significant public health threat.

One of the commonly known antibiotic resistant bacteria includes *Mycobacterium tuberculosis*, the etiological agent of tuberculosis, which continues to be a leading killer world-wide. Despite availability of effective antibiotic regimens, the last decade has seen increasing incidence of drug resistance in human infected with *Mycobacterium tuberculosis*. World Health Organization (WHO) data indicates that almost 300,000 of the new tuberculosis cases are associated with multi- and extensively drug resistant (MDR and XDR, respectively) strains of *Mycobacterium tuberculosis*. Accordingly, it is desirable to design or invent new strategies to control infection with drug resistant mycobacteria. One such strategy could be methods or compounds that enhance the host immune system.

SUMMARY OF THE INVENTION

In one aspect, there is provided a method of preventing, treating or inhibiting bacterial infections. The method comprises administering at least one of the compounds selected from the group consisting of: N,N-dimethyl imidodicarbonimidic diamide hydrochloride (Metformin); 3,5,4'-trihydroxy-trans-stilbene (Resveratrol); methyl 2,6-dimethyl-5-nitro-4-[2-(trifluoromethyl)phenyl]-1,4-dihydropyridine-3-carboxylate (Bay K8644); 2,5-Dimethyl-4-[2-(phenylmethyl)benzoyl]-1H-pyrrole-3-carboxylic acid methyl ester (FPL 64176); 2',5'-Dideoxyadenosine (2'5'-ddA); 4-[4-(4-chlorophenyl)-4-hydroxypiperidin-1-yl]-N,N-dimethyl-2,2-diphenylbutanamide hydrochloride (Loperamide); (5R,6S,8S)-Hexyl 6-hydroxy-5-methyl-13-oxo-6,7,8,13,14,15-hexahydro-5H-16-oxa-4b,8a,14-triaza-5,8-methanodibenzo[b,h]cycloocta[jkl]cyclopenta[e]-as-indacene-6-carboxylate (KT 5720); N-(dicyclopropylmethyl)-4,5-dihydro-1,3-oxazol-2-amine (Rilmenidine); 3-(2-methoxyethyl) 5-propan-2-yl 2,6-dimethyl-4-(3-nitrophenyl)-1,4-dihydropyridine-3,5-dicarboxylate (Nimodipine); (RS)-ethyl methyl 2,6-dimethyl-4-(3-nitrophenyl)-1,4-dihydropyridine-3,5-dicarboxylate (Nitrendipine); (RS)-2-(3,4-dimethoxyphenyl)-5-{[2-(3,4-dimethoxyphenyl)ethyl]-(methyl)amino}-2-prop-2-ylpentanenitrile (Verapamil); (2-{4-[(2-butyl-1-benzofuran-3-yl)carbonyl]-2,6-diiodophenoxy}ethyl)diethylamine (Amiodarone); and [(2R,3S,4R,5R)-5-(4-Carbamoyl-5-aminoimidazol-1-yl)-3,4-dihydroxyoxolan-2-yl]methyl dihydrogen phosphate (AICAR), to a patient in need thereof.

In another aspect, there is provided a method of increasing mitochondrial reactive oxygen species (mROS) generation to inhibit bacterial growth in a cell. The method comprises contacting the infected cell with at least one of the compounds selected from the group consisting of: N,N-dimethyl imidodicarbonimidic diamide hydrochloride (Metformin); 3,5,4'-trihydroxy-trans-stilbene (Resveratrol); methyl 2,6-dimethyl-5-nitro-4-[2-(trifluoromethyl)phenyl]-1,4-dihydropyridine-3-carboxylate (Bay K8644); 2,5-Dimethyl-4-[2-(phenylmethyl)benzoyl]-1H-pyrrole-3-carboxylic acid methyl ester (FPL 64176); 2',5'-Dideoxyadenosine; 4-[4-(4-chlorophenyl)-4-hydroxypiperidin-1-yl]-N,N-dimethyl-2,2-diphenylbutanamide hydrochloride (Loperamide); (5R,6S,8S)-Hexyl 6-hydroxy-5-methyl-13-oxo-6,7,8,13,14,15-hexahydro-5H-16-oxa-4b,8a,14-triaza-5,8-methanodibenzo[b,h]cycloocta[jkl]cyclopenta[e]-as-indacene-6-carboxylate (KT 5720); N-(dicyclopropylmethyl)-4,5-dihydro-1,3-oxazol-2-amine (Rilmenidine); 3-(2-methoxyethyl) 5-propan-2-yl 2,6-dimethyl-4-(3-nitrophenyl)-1,4-dihydropyridine-3,5-dicarboxylate (Nimodipine); (RS)-ethyl methyl 2,6-dimethyl-4-(3-nitrophenyl)-1,4-dihydropyridine-3,5-dicarboxylate (Nitrendipine); (RS)-2-(3,4-dimethoxyphenyl)-5-{[2-(3,4-dimethoxyphenyl)ethyl]-(methyl)amino}-2-prop-2-ylpentanenitrile (Verapamil); (2-{4-[(2-butyl-1-benzofuran-3-yl)carbonyl]-2,6-diiodophenoxy}ethyl)diethylamine (Amiodarone); and [(2R,3S,4R,5R)-5-(4-Carbamoyl-5-aminoimidazol-1-yl)-3,4-dihydroxyoxolan-2-yl]methyl dihydrogen phosphate (AICAR).

In another aspect, there is provided a method of increasing the acidity of bacterial phagosomes to inhibit bacterial growth in a cell. The method comprises contacting the infected cell with at least one of the compounds selected from the group consisting of: N,N-dimethyl imidodicarbonimidic diamide hydrochloride (Metformin); 3,5,4'-trihydroxy-trans-stilbene (Resveratrol); methyl 2,6-dimethyl-5-nitro-4-[2-(trifluoromethyl)phenyl]-1,4-dihydropyridine-3-carboxylate (Bay K8644); 2,5-Dimethyl-4-[2-(phenylmethyl)benzoyl]-1H-pyrrole-3-carboxylic acid methyl ester (FPL 64176); 2',5'-Dideoxyadenosine; 4-[4-(4-chlorophenyl)-4-hydroxypiperidin-1-yl]-N,N-dimethyl-2,2-diphenylbutanamide hydrochloride (Loperamide); (5R,6S,8S)-Hexyl 6-hydroxy-5-methyl-13-oxo-6,7,8,13,14,15-hexahydro-5H-16-oxa-4b,8a,14-triaza-5,8-methanodibenzo[b,h]cycloocta[jkl]cyclopenta[e]-as-indacene-6-carboxylate (KT 5720); N-(dicyclopropylmethyl)-4,5-dihydro-1,3-oxazol-2-amine (Rilmenidine); 3-(2-methoxyethyl) 5-propan- 2-yl 2,6-dimethyl-4-(3-nitrophenyl)-1,4-dihydropyridine-3,5-dicarboxylate (Nimodipine); (RS)-ethyl methyl 2,6-dimethyl-4-(3-nitrophenyl)-1,4-dihydropyridine-3,5-dicarboxylate (Nitrendipine); (RS)-2-(3,4-dimethoxyphenyl)-5-{[2-(3,4-dimethoxyphenyl)ethyl]-(methyl)amino}-2-prop-2-ylpentanenitrile (Verapamil); (2-{4-[(2-butyl-1-benzofuran-3-yl)carbonyl]-2,6-diiodophenoxy}ethyl)diethylamine (Amiodarone); and [(2R,3S,4R,5R)-5-(4-Carbamoyl-5-aminoimidazol-1-yl)-3,4-dihydroxyoxolan-2-yl]methyl dihydrogen phosphate (AICAR).

In another aspect, there is provided a pharmaceutical composition comprising at least one of the compounds selected from the group consisting of N,N-dimethyl imidodicarbonimidic diamide hydrochloride (Metformin); 3,5,4'-trihydroxy-trans-stilbene (Resveratrol); methyl 2,6-dimethyl-5-nitro-4-[2-(trifluoromethyl)phenyl]-1,4-dihydropyridine-3-carboxylate (Bay K8644); 2,5-Dimethyl-4-[2-(phenylmethyl)benzoyl]-1H-pyrrole-3-carboxylic acid methyl ester (FPL 64176); 2',5'-Dideoxyadenosine; 4-[4-(4-chlorophenyl)-4-hydroxypiperidin-1-yl]-N,N-dimethyl-2,2-diphenylbutanamide hydrochloride (Loperamide); (5R,6S,8S)-Hexyl 6-hydroxy-5-methyl-13-oxo-6,7,8,13,14,15-hexahydro-5H-16-oxa-4b,8a,14-triaza-5,8-methanodibenzo[b,h]cycloocta[jkl]cyclopenta[e]-as-indacene-6-carboxylate (KT 5720); N-(dicyclopropylmethyl)-4,5-dihydro-1,3-oxazol-2-amine (Rilmenidine); 3-(2-methoxyethyl) 5-propan-2-yl 2,6-dimethyl-4-(3-nitrophenyl)-1,4-dihydropyridine-3,5-dicarboxylate (Nimodipine); (RS)-ethyl methyl 2,6-dimethyl-4-(3-nitrophenyl)-1,4-dihydropyridine-3,5-dicarboxylate (Nitrendipine); (RS)-2-(3,4-dimethoxyphenyl)-5-{[2-(3,4-dimethoxyphenyl)ethyl]-(methyl)amino}-2-prop-2-ylpentanenitrile (Verapamil); (2-{4-[(2-butyl-1-benzofuran-3-yl)carbonyl]-2,6-diiodophenoxy}ethyl)diethylamine (Amiodarone); and [(2R,3S,4R,5R)-5-(4-Carbamoyl-5-aminoimidazol-1-yl)-3,4-dihydroxyoxolan-2-yl]methyl dihydrogen phosphate (AICAR). The pharmaceutical composition may optionally comprise an anti-tuberculosis drug. The pharmaceutical composition may optionally comprise a pharmaceutically acceptable excipient.

In one aspect, there is provided a use of at least one of the compounds selected from the group consisting of: N,N-dimethyl imidodicarbonimidic diamide hydrochloride (Metformin); 3,5,4'-trihydroxy-trans-stilbene (Resveratrol); methyl 2,6-dimethyl-5-nitro-4-[2-(trifluoromethyl)phenyl]-1,4-dihydropyridine-3-carboxylate (Bay K8644); 2,5-Dimethyl-4-[2-(phenylmethyl)benzoyl]-1H-pyrrole-3-carboxylic acid methyl ester (FPL 64176); 2',5'-Dideoxyadenosine; 4-[4-(4-chlorophenyl)-4-hydroxypiperidin-1-yl]-N,N-dimethyl-2,2-diphenylbutanamide hydrochloride (Loperamide); (5R,6S,8S)-Hexyl 6-hydroxy-5-methyl-13-oxo-6,7,8,13,14,15-hexahydro-5H-16-oxa-4b,8a,14-triaza-5,8-methanodibenzo[b,h]cycloocta[jkl]cyclopenta[e]-as-indacene-6-carboxylate (KT 5720); N-(dicyclopropylmethyl)-4,5-dihydro-1,3-oxazol-2-amine (Rilmenidine); 3,5,4'-trihydroxy-trans-stilbene (Resveratrol); 3-(2-methoxyethyl) 5-propan-2-yl 2,6-dimethyl-4-(3-nitrophenyl)-1,4-dihydropyridine-3,5-dicarboxylate (Nimodipine); (RS)-ethyl methyl 2,6-dimethyl-4-(3-nitrophenyl)-1,4-dihydropyridine-3,5-dicarboxylate (Nitrendipine); (RS)-2-(3,4-dimethoxyphenyl)-5-{[2-(3,4-dimethoxyphenyl)ethyl]-(methyl)amino}-2-prop-2-ylpentanenitrile (Verapamil); (2-{4-[(2-butyl-1-benzofuran-3-yl)carbonyl]-2,6-diiodophenoxy}ethyl)diethylamine (Amiodarone); and [(2R,3S,4R,5R)-5-(4-Carbamoyl-5-aminoimidazol-1-yl)-3,4-dihydroxyoxolan-2-yl]methyl dihydrogen phosphate (AICAR), in the manufacture of a medicament to prevent, treat or inhibit bacterial infections.

In another aspect, there is provided a use of at least one of the compounds selected from the group consisting of: N,N-dimethyl imidodicarbonimidic diamide hydrochloride (Metformin); 3,5,4'-trihydroxy-trans-stilbene (Resveratrol); methyl 2,6-dimethyl-5-nitro-4-[2-(trifluoromethyl)phenyl]-1,4-dihydropyridine-3-carboxylate (Bay K8644); 2,5-Dimethyl-4-[2-(phenylmethyl)benzoyl]-1H-pyrrole-3-carboxylic acid methyl ester (FPL 64176); 2',5'-Dideoxyadenosine; 4-[4-(4-chlorophenyl)-4-hydroxypiperidin-1-yl]-N,N-dimethyl-2,2-diphenylbutanamide hydrochloride (Loperamide); (5R,6S,8S)-Hexyl 6-hydroxy-5-methyl-13-oxo-6,7,8,13,14,15-hexahydro-5H-16-oxa-4b,8a,14-triaza-5,8-methanodibenzo[b,h]cycloocta[jkl]cyclopenta[e]-as-indacene-6-carboxylate (KT 5720); N-(dicyclopropylmethyl)-4,5-dihydro-1,3-oxazol-2-amine (Rilmenidine); 3-(2-methoxyethyl) 5-propan-2-yl 2,6-dimethyl-4-(3-nitrophenyl)-1,4-dihydropyridine-3,5-dicarboxylate (Nimodipine); (RS)-ethyl methyl 2,6-dimethyl-4-(3-nitrophenyl)-1,4-dihydropyridine-3,5-dicarboxylate (Nitrendipine); (RS)-2-(3,4-dimethoxyphenyl)-5-{[2-(3,4-dimethoxyphenyl)ethyl]-(methyl)amino}-2-prop-2-ylpentanenitrile (Verapamil); (2-{4-[(2-butyl-1-benzofuran-3-yl)carbonyl]-2,6-diiodophenoxy}ethyl)diethylamine (Amiodarone); and [(2R,3S,4R,5R)-5-(4-Carbamoyl-5-aminoimidazol-1-yl)-3,4-dihydroxyoxolan-2-yl]methyl dihydrogen phosphate (AICAR), in combination with an anti-tuberculosis drug in the manufacture of a medicament to prevent, treat or inhibit mycobacterial infections.

In another aspect, there is provided a use of at least one of the compounds selected from the group consisting of: N,N-dimethyl imidodicarbonimidic diamide hydrochloride (Metformin); 3,5,4'-trihydroxy-trans-stilbene (Resveratrol); methyl 2,6-dimethyl-5-nitro-4-[2-(trifluoromethyl)phenyl]-1,4-dihydropyridine-3-carboxylate (Bay K8644); 2,5-Dimethyl-4-[2-(phenylmethyl)benzoyl]-1H-pyrrole-3-carboxylic acid methyl ester (FPL 64176); 2',5'-Dideoxyadenosine; 4-[4-(4-chlorophenyl)-4-hydroxypiperidin-1-yl]-N,N-dimethyl-2,2-diphenylbutanamide hydrochloride (Loperamide); (5R,6S,8S)-Hexyl 6-hydroxy-5-methyl-13-oxo-6,7,8,13,14,15-hexahydro-5H-16-oxa-4b,8a,14-triaza-5,8-methanodibenzo[b,h]cycloocta[jkl]cyclopenta[e]-as-indacene-6-carboxylate (KT 5720); N-(dicyclopropylmethyl)-4,5-dihydro-1,3-oxazol-2-amine (Rilmenidine); 3-(2-methoxyethyl) 5-propan-2-yl 2,6-dimethyl-4-(3-nitrophenyl)-1,4-dihydropyridine-3,5-dicarboxylate (Nimodipine); (RS)-ethyl methyl 2,6-dimethyl-4-(3-nitrophenyl)-1,4-dihydropyridine-3,5-dicarboxylate (Nitrendipine); (RS)-2-(3,4-dimethoxyphenyl)-5-{[2-(3,4-dimethoxyphenyl)ethyl]-(methyl)amino}-2-prop-2-ylpentanenitrile (Verapamil); (2-{4-[(2-butyl-1-benzofuran-3-yl)carbonyl]-2,6-diiodophenoxy}ethyl)diethylamine (Amiodarone); and [(2R,3S,4R,5R)-5-(4-Carbamoyl-5-aminoimidazol-1-yl)-3,4-dihydroxyoxolan-2-yl]methyl dihydrogen phosphate (AICAR), in the manufacture of a medicament to inhibit bacterial growth in a cell.

In another aspect, there is provided a method for eliciting an immune response to intracellular bacteria. The method comprises administering at least one compound selected from the group consisting of: N,N-dimethyl imidodicarbonimidic diamide hydrochloride (Metformin); 3,5,4'-trihydroxy-trans-stilbene (Resveratrol); methyl 2,6-dimethyl-5-nitro-4-[2-(trifluoromethyl)phenyl]-1,4-dihydropyridine-3-carboxylate (Bay K8644); 2,5-Dimethyl-4-[2-(phenylmethyl)benzoyl]-1H-pyrrole-3-carboxylic acid methyl ester (FPL 64176); 2',5'-Dideoxyadenosine; 4-[4-(4- chlorophenyl)-4-hydroxypiperidin-1-yl]-N,N-dimethyl-2,2-diphenylbutanamide hydrochloride (Loperamide); (5R,6S,8S)-Hexyl 6-hydroxy-5-methyl-13-oxo-6,7,8,13,14,15-hexahydro-5H-16-oxa-4b,8a,14-triaza-5,8-methanodibenzo[b,h]cycloocta[jkl]cyclopenta[e]-as-indacene-6-carboxylate (KT 5720); N-(dicyclopropylmethyl)-4,5-dihydro-1,3-oxazol-2-amine (Rilmenidine); 3-(2-methoxyethyl) 5-propan-2-yl 2,6-dimethyl-4-(3-nitrophenyl)-1,4-dihydropyridine-3,5-dicarboxylate (Nimodipine); (RS)-ethyl methyl 2,6-dimethyl-4-(3-nitrophenyl)-1,4-dihydropyridine-3,5-dicarboxylate (Nitrendipine); (RS)-2-(3,4-dimethoxyphenyl)-5-{[2-(3,4-dimethoxyphenyl)ethyl]-(methyl)amino}-2-prop-2-ylpentanenitrile (Verapamil); (2-{4-[(2-butyl-1-benzofuran-3-yl)carbonyl]-2,6-diiodophenoxy}ethyl)diethylamine (Amiodarone); and [(2R,3S,4R,5R)-5-(4-Carbamoyl-5-aminoimidazol-1-yl)-3,4-dihydroxyoxolan-2-yl]methyl dihydrogen phosphate (AICAR).

BRIEF DESCRIPTION OF THE DRAWINGS

The invention will be better understood with reference to the detailed description when considered in conjunction with the non-limiting examples and the accompanying drawings, in which:

FIG. 1 shows significant inhibition of intracellular mycobacterial growth by 10 of the compounds out of 16 tested.

FIG. 2 demonstrates that all compounds except amiodarone as described in the present disclosure do not have any direct anti-mycobacterial activity.

FIG. 4 shows Metformin induces mitochondrial reactive oxygen species production.

FIG. 6 shows scavenging reactive oxygen species abolishes Metformin-induced mROS production as well as inhibition of mycobacterial growth.

FIG. 9 shows Metformin inhibits growth of intracellular *Mycobacterium tuberculosis* in dose-dependent manner.

FIG. 10 shows scavenging ROS abolishes Metformin-induced inhibition of MTB growth.

FIG. 12 shows Metformin enhances the efficacy of Isoniazid.

FIG. 13 demonstrates that Metformin enhances the efficacy of ethionamide.

FIG. 14 shows Metformin is capable of inhibiting dissemination of *Mycobacterium tuberculosis* from lung to the spleen of mice.

FIG. 15 shows Metformin enhances the bactericidal activity of ethionamide in the spleen of mice.

DETAILED DESCRIPTION OF THE PRESENT INVENTION

Figure 1:
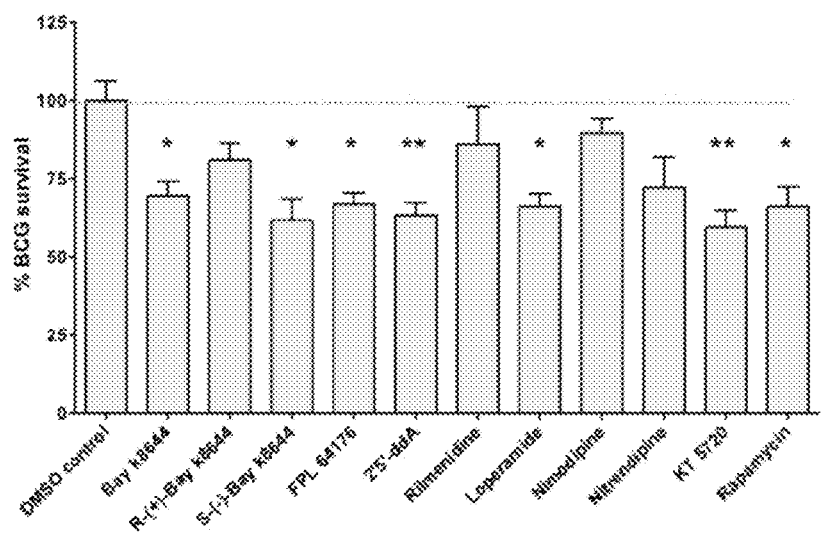
FIG. 1 shows bar graphs of inhibition of intracellular mycobacterial growth by experimental compounds. THP1 cells were infected with *Mycobacterium bovis* BCG with a multiplicity of infection (MOI) of 5 for 3 hrs. Infected cells were washed to remove extracellular bacteria and were either treated with 0.1% DMSO (negative control) or with indicated compounds for 24 hrs. After 24 hrs cells were lysed for mycobacterial viability determination using colony forming unit (CFU) assay. In these assays Rapamycin was used as a positive control as its efficacy on intracellular mycobacteria has been shown earlier. (A) Shows inhibition by 1 µM of indicated compounds; (B) Shows inhibition by 10 µM of indicated compounds; (C) Shows inhibition by 100 µM of indicated compounds. Results are expressed as percentage (%) of BCG survival in cells treated with compounds compared to control. Values are expressed as mean±SEM. *, $p<0.05$; **, $p<0.01$, Student's t-test.
Figure 1:
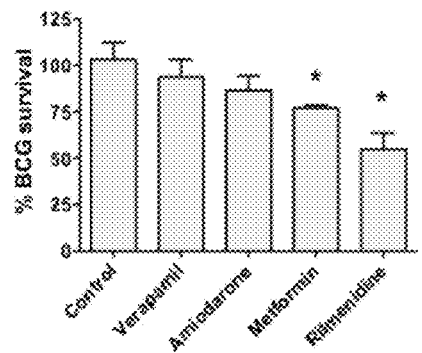
Figure 1:
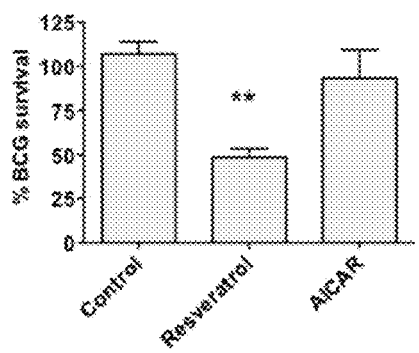

As pathogen-targeted strategy has the serious disadvantage of drug resistance development, new therapeutic approaches have been invoked. A new paradigm in drug discovery involves targeting host cellular factors that are modulated or hijacked by the pathogen for its survival. This host-directed approach would be able to control not only drug-susceptible but also drug-resistant bacterial infections. This is because, such strategies boost host immunity instead of directly targeting pathogens and therefore they are less likely to induce microbial resistance. Accordingly, there is provided a method for eliciting an immune response to intracellular bacteria.

As used herein, the term "elicit" refers to the act of drawing forth, initiating or evoking an immune response in the mammal. The term "elicit" in the present disclosure may be used as a synonym of "enhancing".

As used herein, the term "immune response" refers to the system of biological structures and processes within an organism that protects against disease.

In one example, the elicitation or enhancement of immune response in the present disclosure refers to the improvement in phagocytic cell functions such as, but not limited to, increased production of oxidative substances such as, but not limited to, superoxide radical, hydrogen peroxide, and combinations thereof. For example, without wishing to be bound by theory, it is believed that phagosomes containing *mycobacterium* are less acidic than neighboring phagosomes. Accordingly, the inventors of the present disclosure discovered a method of reversing the reduced acidity in phagosomes infected by *mycobacterium*. In one example, the improvement in phagocytic cells function includes, but not limited to, increase in acidity of bacterial phagosomes in phagocytic cells and increase in mitochondrial reactive oxygen species (mROS) generation. Exemplary elicitation of immune system includes increased acidity of bacterial phagosomes in phagocytic cell as illustrated in Example 4 and increase in mitochondrial reactive oxygen species (mROS) generation as illustrated in Examples 3 and 5.

In one example, the phagocytic cell may be a macrophage. In one example, the phagocytic cell may be an alveolar macrophage, macrophage found in the lung. In one example, the phagocytic cell may be found in the spleen.

Also disclosed is a method of increasing the acidity of bacterial phagosomes to inhibit bacterial growth in a cell. As used herein, the term "phagosomes" refers to a membrane-bound vesicle formed around a foreign matter, wherein the vesicle is formed through a process of phagocytosis. In one example, the foreign matter is a bacterium or plurality of bacteria absorbed by phagocytosis. Thus, the phrase "bacterial phagosome" refers to a vesicle or a cellular compartment in which a bacterium or bacteria can be killed and digested.

As used herein, the term "increased", "increasing", "increase" or any other grammatical variants thereof refer to greater amount, intensity, or degree relative to an untreated control. The increased in expression may be at least about 5%, 10%, 15%, 20%, 25%, 30%, 35%, 40%, 45%, 50%, 55%, 60%, 65%, 70%, 75%, 80%, 85%, 90%, 95% or 100% more than that of an untreated control.

Also disclosed is a method of preventing, treating or inhibiting bacterial infection. The terms "treat," "treatment," and grammatical variants thereof, refer to both therapeutic treatment and prophylactic or preventative measures, wherein the object is to prevent or slow down (lessen) an undesired physiological condition, disorder or disease or obtain beneficial or desired clinical results. Such beneficial or desired clinical results include, but are not limited to, alleviation of symptoms; diminishment of extent of condition, disorder or disease; stabilized (i.e. not worsening) state of condition, disorder or disease; delay or slowing of condition, disorder or disease progression; amelioration of the condition, disorder or disease state, remission (whether partial or total), whether detectable or undetectable; or enhancement or improvement of condition, disorder or disease. Treatment includes eliciting a cellular response that is clinically significant, without excessive levels of side effects. Treatment also includes prolonging survival as compared to expected survival if not receiving treatment.

In one example, the methods as described herein comprise administering at least 1, 2, 3, 4, 5, 6, 7, 8, 9, 10, 11, 12 or all of the compounds of the present disclosure into a patient in need thereof.

In one example, the compounds of the present disclosure includes, but is not limited to N,N-dimethyl imidodicarbonimidic diamide hydrochloride (Metformin); 3,5,4'-trihydroxy-trans-stilbene (Resveratrol); methyl 2,6-dimethyl-5-nitro-4-[2-(trifluoromethyl)phenyl]-1,4-dihydropyridine-3-carboxylate (Bay K8644); 2,5-Dimethyl-4-[2-(phenylmethyl)benzoyl]-1H-pyrrole-3-carboxylic acid methyl ester (FPL 64176); 2',5'-Dideoxyadenosine; 4-[4-(4-chlorophenyl)-4-hydroxypiperidin-1-yl]-N,N-dimethyl-2,2-diphenylbutanamide hydrochloride (Loperamide); (5R,6S,8S)-Hexyl 6-hydroxy-5-methyl-13-oxo-6,7,8,13,14,15-hexahydro-5H-16-oxa-4b,8a,14-triaza-5,8-methanodibenzo[b,h]cycloocta[jkl]cyclopenta[e]-as-indacene-6-carboxylate (KT 5720); N-(dicyclopropylmethyl)-4,5-dihydro-1,3-oxazol-2-amine (Rilmenidine); 3-(2-methoxyethyl) 5-propan-2-yl 2,6-dimethyl-4-(3-nitrophenyl)-1,4-dihydropyridine-3,5-dicarboxylate (Nimodipine); (RS)-ethyl methyl 2,6-dimethyl-4-(3-nitrophenyl)-1,4-dihydropyridine-3,5-dicarboxylate (Nitrendipine); (RS)-2-(3,4-dimethoxyphenyl)-5-{[2-(3,4-dimethoxyphenyl)ethyl]-(methyl)amino}-2-prop-2-ylpentanenitrile (Verapamil); (2-{4-[(2-butyl-1-benzofuran-3-yl)carbonyl]-2,6-diiodophenoxy}ethyl)diethylamine (Amiodarone); and

[(2R,3S,4R,5R)-5-(4-Carbamoyl-5-aminoimidazol-1-yl)-3,4-dihydroxyoxolan-2-yl]methyl dihydrogen phosphate (AICAR).

In one example, the methyl 2,6-dimethyl-5-nitro-4-[2-(trifluoromethyl)phenyl]-1,4-dihydropyridine-3-carboxylate (Bay K8644) may be S-(+)-methyl 2,6-dimethyl-5-nitro-4-[2-(trifluoromethyl)phenyl]-1,4-dihydropyridine-3-carboxylate (Bay K8644).

In one example, the compounds may be N,N-dimethyl imidodicarbonimidic diamide hydrochloride (Metformin) and 3,5,4'-trihydroxy-trans-stilbene (Resveratrol).

In one example, the methods as described herein may further comprise administering an anti-tuberculosis drug together or separately. In one example, the anti-tuberculosis drug may include, but is not limited to isoniazid, pyrazinamide, rifampicin, ethionamide, rifabutin, amikacin, ethambutol, PA824, bedaquiline, streptomycin, kanamycin and fluoroquinolone antibiotic or their combinations as additional anti-TB agents.

Also disclosed is a pharmaceutical composition comprising at least 1, 2, 3, 4, 5, 6, 7, 8, 9, 10, 11, 12 or all of the compounds of the present disclosure. In one example, the pharmaceutical composition may include an anti-tuberculosis drug. In one example, the pharmaceutical composition may optionally include a pharmaceutically acceptable excipient. As used herein, the term "pharmaceutically acceptable" is given its ordinary meaning. Pharmaceutically acceptable compositions are generally compatible with other materials of the formulation and are not generally deleterious to the patient.

Also disclosed is the use of at least 1, 2, 3, 4, 5, 6, 7, 8, 9, 10, 11, 12 or all of the compounds as described herein in the manufacture of a medicament to prevent, treat or inhibit bacterial infections.

Also disclosed is the use of at least 1, 2, 3, 4, 5, 6, 7, 8, 9, 10, 11, 12 or all of the compounds as described herein in the manufacture of a medicament to prevent, treat or inhibit mycobacterial infections. In one example, the compounds may be administered together or separately with the anti-tuberculosis drug. In one example, the medicament as described herein may further comprise an anti-tuberculosis drug to be administered to the patient together or separately from the compounds as described herein. Accordingly, in one example, there is provided the use of at least 1, 2, 3, 4, 5, 6, 7, 8, 9, 10, 11, 12 or all of the compounds as described herein in combination with an anti-tuberculosis drug in the manufacture of a medicament to prevent, treat or inhibit mycobacterial infections.

Also disclosed is the use of at least 1, 2, 3, 4, 5, 6, 7, 8, 9, 10, 11, 12 or all of the compounds as described herein in the manufacture of a medicament to inhibit bacterial growth in a cell.

As used herein, "an anti-tuberculosis drug" refers to agents, compounds or compositions known to be useful in treating tuberculosis in a patient. In one example, the anti-tuberculosis drug may include, but not limited to isonicotinohydrazide (Isoniazid), 5-(2,4-diguanidino-3,5,6-trihydroxy-cyclohexoxy)-4-[4,5-dihydroxy-6-(hydroxymethyl)-3-methylamino-tetrahydropyran-2-yl]oxy-3-hydroxy-2-methyl-tetrahydrofuran-3-carbaldehyde (streptomycin), pyrazine-2-carboxamide (Pyrazinamide), (7S,9E,11S,12R,13S,14R,15R,16R,17S,18S,19E,21Z)-2,15,17,27,29-pentahydroxy-11-methoxy-3,7,12,14,16,18,22-heptamethyl-26-{(E)-[(4-methylpiperazin-1-yl)imino]methyl}-6,23-dioxo-8,30-dioxa-24-azatetracyclo[23.3.1.14,7.05,28]triaconta1(28),2,4,9,19,21,25(29),26-octaen-13-yl acetate (Rifampicin), (9S,12E,14S,15R,16S,17R,18R,19R,20S,21S,22E,24Z)-6,16,18,20-tetrahydroxy-1-isobutyl-14-methoxy-7,9,15,17,19,21,25-hepta-methyl-spiro[9,4-(epoxypentadeca[1,11,13]trienimino)-2H-furo-[2',3':7,8]-naphth[1,2-d]imidazol-2,4'-piperidin]-5,10,26-(3H,9H)-trione-16-acetate (Rifabutin), (2S)-4-amino-N-[(2S,3S,4R,5S)-5-amino-2-[(2S,3R,4S,5S,6R)-4-amino-3,5-dihydroxy-6-(hydroxymethyl)oxan-2-yl]oxy-4-[(2R,3R,4S,5R,6R)-6-(aminomethyl)-3,4,5-trihydroxy-oxan-2-yl]oxy-3-hydroxy-cyclohexyl]-2-hydroxy-butanamide (Amikacin), (2S,2'S)-2,2'-(Ethane-1,2-diyldiimino)dibutan-1-ol (Ethambutol), 2-ethylpyridine-4-carbothioamide (Ethionamide), (6S)-2-nitro-6-{[4-(trifluoromethoxy)benzyl]oxy}-6,7-dihydro-5H-imidazo[2,1-b][1,3]oxazine (PA824), (1R,2S)-1-(6-Bromo-2-methoxy-3-quinolyl)-4-dimethylamino-2-(1-naphthyl)-1-phenyl-butan-2-ol (Bedaquiline), 2-(aminomethyl)-6-[4,6-diamino-3-[4-amino-3,5-dihydroxy-6-(hydroxymethyl)tetrahydropyran-2-yl]oxy-2-hydroxy-cyclohexoxy]-tetrahydropyran-3,4,5-triol (Kanamycin), 1-cyclopropyl-7-[(1S,6S)-2,8-diazabicyclo[4.3.0]non-8-yl]-6-fluoro-8-methoxy-4-oxo-quinoline-3-carboxylic acid (Moxifloxacin), (S)—N-({3-[3-fluoro-4-(morpholin-4-yl)phenyl]-2-oxo-1,3-oxazolidin-5-yl}methyl)acetamide (Linezolid) and Fluoroquinolone antibiotic or their combinations thereof. As illustrated by Examples 6, 7, and 8, when used in combination with an anti-tuberculosis drug, the compounds as described herein enhances the efficacy of the known anti-tuberculosis drug.

In one example, the methods as described herein comprises administering N,N-dimethyl imidodicarbonimidic diamide hydrochloride (Metformin) in combination with isoniazid, which is exemplified by Example 6. In one example, the method as described herein comprises administering 3,5,4'-trihydroxy-trans-stilbene (Resveratrol) in combination with isoniazid, which is exemplified by Example 8.

In one example, the methods or medicaments as described herein may further comprise a second therapeutic agent. The second therapeutic agent may include, but not limited to, Ampicillin, Bacampicillin, Carbenicillin Indanyl, Mezlocillin, Piperacillin, Ticarcillin, Amoxicillin-Clavulanic Acid, Ampicillin-Sulbactam, Benzylpenicillin, Cloxacillin, Dicloxacillin, Methicillin, Oxacillin, Penicillin G, Penicillin V, Piperacillin Tazobactam, Ticarcillin Clavulanic Acid, Nafcillin, Cephalosporin I Generation, Cefadroxil, Cefazolin, Cephalexin, Cephalothin, Cephapirin, Cephradine, Cefaclor, Cefamandol, Cefonicid, Cefotetan, Cefoxitin, Cefprozil, Ceftmetazole, Cefuroxime, Loracarbef, Cefdinir, Ceftibuten, Cefoperazone, Cefixime, Cefotaxime, Cefpodoxime proxetil, Ceftazidime, Ceftizoxime, Ceftriaxone, Cefepime, Azithromycin, Clarithromycin, Clindamycin, Dirithromycin, Erythromycin, Lincomycin, Troleandomycin, Cinoxacin, Ciprofloxacin, Enoxacin, Gatifloxacin, Grepafloxacin, Levofloxacin, Lomefloxacin, Moxifloxacin, Nalidixic acid, Norfloxacin, Ofloxacin, Sparfloxacin, Trovafloxacin, Oxolinic acid, Gemifloxacin, Pefloxacin, Imipenem-Cilastatin, Meropenem, Aztreonam, Amikacin, Gentamicin, Kanamycin, Neomycin, Netilmicin, Streptomycin, Tobramycin, Paromomycin, Teicoplanin, Vancomycin, Demeclocycline, Doxycycline, Methacycline, Minocycline, Oxytetracycline, Tetracycline, Chlortetracycline, Mafenide, Silver Sulfadiazine, Sulfacetamide, Sulfadiazine, Sulfamethoxazole, Sulfasalazine, Sulfisoxazole, Trimethoprim-Sulfamethoxazole, Sulfamethizole, Rifabutin, Rifampin, Rifapentine, Linezolid, Streptogramins, Quinopristin Dalfopristin, Bacitracin, Chloramphenicol, Fosfomycin, ISoniazid, Methenamine, Metronidazol, Mupirocin, Nitrofurantoin, Nitrofurazone, Novobiocin, Polymyxin, Spectinomycin, Trimethoprim, Colistin, Cycloserine, Capreomycin, Ethionamide, Pyrazinamide, Para-aminosalicyclic acid, Erythromycin ethylsuccinate, Miconazole, Ketoconazole, Clotrimazole, Econazole, Bifonazole, Butoconazole, Fenticonazole, Isoconazole, Oxiconazole, Sertaconazole, Sulconazole, Tioconazole, Fluconazole, Itraconazole, Isavuconazole, Ravuconazole, Posaconazole, Voriconazole, Terconazole, Terbinafine, Amorolfine, Naftifine, Butenafine, Anidulafungin, Caspofungin, Micafungin, Benzoic acid, Ciclopirox, Tolnaftate, Undecylenic acid, Flucytosine, or 5-fluorocytosine, Griseofulvin, Haloprogin and combinations thereof.

In one example, the methods as described herein comprises administering N,N-dimethyl imidodicarbonimidic diamide hydrochloride (Metformin) in combination with ethionamide. Exemplary disclosure of the method as described herein demonstrating the enhanced efficacy of ethionamide is observed Example 7.

In one example, the patient may be an animal, mammal, human, including, without limitation, animals classed as bovine, porcine, equine, canine, lupine, feline, murine, ovine, avian, piscine, caprine, corvine, acrine, or delphine. In one example, the patient may be a human.

Bacterial infections that may be treated include, but not limited to, those caused by *Acetobacter aurantius, Acinetobacter baumannii, Actinomyces Israelii, Agrobacterium* spp. (such as *A. radiobacter, A. tumefaciens*), *Azorhizobium caulinodans, Azotobacter vinelandii, Anaplasma* spp. (such as *A. phagocytophilum, A. marginale*), *Bacillus* spp. (such as *B. anthracis, B. brevis, B. cereus, B. fusiformis, B. licheniformis, B. megaterium, B. mycoides, B. stearothermophilus, B. subtilis*), *Bacteroides* spp. (such as *B. fragilis, B. gingivalis, B. melaminogenicus* (now known as *Prevotella melaminogenica*)), *Bartonella* spp. (such as *B. henselae, B. quintana*), *Bordetella* spp. (such as *B. bronchiseptica, B. pertussis*), *Borrelia burgdorferi, Brucella* spp. (such as *B. abortus, B. melitensis, B. suis*), *Burkholderia* spp. (such as *B. mallei, B. pseudomallei, B. cepacia* complex, *B. cenocepacia*), *Calymmatobacterium granulomatis, Campylobacter* spp. (such as *C. coli, C. fetus, C. jejuni, C. pylori*), *Chlamydia* spp. (such as *C. trachomatis*), *Chlamydophila* spp. (such as *C. pneumoniae* (previously called *Chlamydia pneumoniae*), *C. psittaci* (previously called *Chlamydia psittaci*)), *Clostridium* spp. (such as *C. botulinum, C. difficile, C. perfringens* (previously called *Clostridium welchii*), *C. tetani*), *Corynebacterium* spp. (such as *C. diphtheriae, C. fusiforme*), *Coxiella bumetii, Ehrlichia chaffeensis, Enterobacter cloacae, Enterococcus* spp. (such as *E. avium, E. durans, E. faecalis, E. faecium, E. galllinarum, E. maloratus*), *Escherichia coli, Francisella tularensis, Fusobacterium nucleatum, Gardnerella vaginalis, Haemophilus* spp. (such as *H. ducreyi, H. influenzae, H. parainfluenzae, H. pertussis, H. vaginalis*), *Helicobacter pylori, Klebsiella pneumoniae, Lactobacillus* spp. (such as *L. acidophilus, L. casei*), *Lactococcus lactis, Legionella pneumophila, Listeria monocytogenes, Methanobacterium extroquens, Microbacterium multiforme, Micrococcus luteus, Moraxella catarrhalis, Mycobacterium* spp. (such as *M. avium, M. bovis, M. diphtheriae, M. intracellulare, M. leprae, M. lepraemurium, M. phlei, M. smegmatis, M. tuberculosis*), *Mycoplasma* spp. (such as *M. fermentans, M. genitalium, M. hominis, M. penetrans, M. pneumoniae*), *Neisseria* spp. (such as *N. gonorrhoeae, N. meningitidis*), *Pasteurella* spp. (such as *P. multocida, P. tularensis*) *Peptostreptococcus, Porphyromonas gingivalis, Pseudomonas aeruginosa, Rhizobium Radiobacter, Rickettsia* spp. (such as *R. prowazekii, R. psittaci, R. quintana, R. rickettsii, R. trachomae*), *Rochalimaea* spp. (such as *R. henselae, R. quintana*), *Rothia dentocariosa, Salmonella* spp. (such as *S. enteritidis, S. typhi, S. typhimurium*), *Serratia marcescens, Shigella dysenteriae, Staphylococcus* spp. (such as *S. aureus, S. epidermidis*), *Stenotrophomonas maltophilia, Streptococcus* spp. (such as *S. agalactiae, S. avium, S. bovis, S. cricetus, S. faceium, S. faecalis, S. ferus, S. gallinarum, S. lactis, S. mitior, S. mitis, S. mutans, S. oralis, S. pneumoniae, S. pyogenes, S. rattus, S. salivarius, S. sanguis, S. sobrinus*), *Treponema* spp. (such as *T. pallidum, T. denticola*), *Vibrio* spp. (such as *V. cholerae, V. comma, V. parahaemolyticus, V. vulnificus*), *Wolbachia*, and/or *Yersinia* spp. (such as *Y. enterocolitica, Y. pestis, Y. pseudotuberculosis*).

In one example, the bacteria is a gram-positive bacteria. In one example, the bacteria is within the phylum of Actinobacteria. In one example, the bacteria is within the order of Actinomycetales. In one example, the bacteria may be in the suborder of Corynebacterineae. In one example, the bacteria may be in the family of Mycobacteriaceae. In one example, the bacteria may be in the genus of mycobacteria. Therefore, the bacterial infection is mycobacterial infection. In one example, the mycobacteria is selected from the groups consisting of *M. tuberculosis, M. bovis, M. bovis* BCG, *M. africanum, M. canetti, M. caprae, M. microti, M. leprae, M. avium, M. paratuberculosis* and *M. pinnipedii*. In one example, the mycobacteria are drug resistant *M. tuberculosis*. As used herein, "drug resistant" refers to the ability for bacteria to survive, multiply, cause disease or damages to the patient despite being in the presence of the antibacterial drug. In one example, the drug resistance may be towards more than one, two, three or more antibacterial drugs i.e. multi-drug resistance (MDR) and/or extremely drug resistance (XDR).

In one example, the bacterial infection may be an intracellular or extracellular bacterial infection. In one example, the bacterial infection may be intracellular bacterial infection. As used herein, the term "intracellular" refers within a patient's cell. Therefore, an "intracellular bacterial infection" refers to infection and/or invasion caused by bacteria where at least part of its reproductive or life cycle exists within a cell of a patient.

The compositions as described herein may be administered in a number of ways depending upon whether local or systemic treatment is desired. Administration may be topical, pulmonary (e.g., by inhalation or insufflation of powders or aerosols, including by nebulizer; intratracheal, intranasal, epidermal and transdermal) or systemic such as oral, and/or parenteral. Parenteral administration includes intravenous, intraarterial, subcutaneous, intraperitoneal or intramuscular injection or infusion; or intracranial, e.g., intrathecal or intraventricular, administration. In one example, the route of administration may be selected from the group consisting of systemic administration, oral administration, intravenous administration and parenteral administration Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Compositions as described herein include, but are not limited to, solutions, emulsions, and liposome-containing formulations. These compositions may be generated from a variety of components that include, but are not limited to, preformed liquids, self-emulsifying solids and self-emulsifying semisolids.

The formulations as described herein, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions as described herein may be formulated into any of many possible dosage forms including, but not limited to tablets, capsules, liquid syrups, soft gels, suppositories, and enemas. The compositions as described herein may also be formulated as suspensions in aqueous, non-aqueous or mixed media. Aqueous suspensions may further contain substances that increase the viscosity of the suspension including, for example, sodium carboxymethyl cellulose, sorbitol and/or dextran. The suspension may also contain stabilizers.

In one example, the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product.

The compositions as described herein may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present disclosure. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

The term "therapeutically effective amount" as used herein includes within its meaning a sufficient but non-toxic amount of the compound as described herein to provide the desired therapeutic effect. The exact amount required will vary from subject to subject depending on factors such as the species being treated, the age and general condition of the subject, the severity of the condition being treated, the particular agent being administered, the mode of administration, and so forth. Thus, it is not possible to specify an exact "effective amount". However, for any given case, an appropriate "effective amount" may be determined by one of ordinary skill in the art using only routine experimentation.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. The administering physician can easily determine optimum dosages, dosing methodologies and repetition rates. Optimum dosages may vary depending on the relative potency of the composition, and can generally be estimated based on EC50s found to be effective in in vitro and in vivo animal models or based on the examples described herein. In general, dosage is from 0.01 μg to 100 g/kg of body weight, and may be given once or more daily, weekly, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, wherein the composition is administered in maintenance doses, ranging from 0.01 μg to 100 g/kg of body weight, once or more daily, to once every 2 years.

In one example, the compound may be administered in an amount of between any one of about 0.01 μg, 0.05 μg, 0.1 μg, 0.5 μg, 1 μg, 5 μg, 10 μg, 20 μg, 30 μg, 40 μg, 50 μg, 60 μg, 70 μg, 80 μg, 90 μg, 100 μg, 110 μg, 120 μg, 130 μg, 140 μg, 150 μg, 160 μg, 170 μg, 180 μg, 190 μg, 200 μg, 210 μg, 220 μg, 230 μg, 240 μg, 250 μg, 260 μg, 270 μg, 280 μg, 290 μg, 500 μg, 1 mg, 1.5 mg, 2 mg, 2.5 mg, 3 mg, 3.5 mg, 4 mg, 5 mg, 10 mg, 15 mg, 20 mg, 25 mg, 30 mg, 35 mg, 40 mg, 45 mg, 50 mg, 75 mg, 100 mg, 125 mg, 150 mg, 175 mg, 200 mg, 225 mg, 250 mg to any one of about 0.01 μg, 0.05 μg, 0.1 μg, 0.5 μg, 1 μg, 5 μg, 10 μg, 20 μg, 30 μg, 40 μg, 50 μg, 60 μg, 70 μg, 80 μg, 90 μg, 100 μg, 110 μg, 120 μg, 130 μg, 140 μg, 150 μg, 160 μg, 170 μg, 180 μg, 190 μg, 200 μg, 210 μg, 220 μg, 230 μg, 240 μg, 250 μg, 260 μg, 270 μg, 280 μg, 290 μg, 500 μg, 1 mg, 1.5 mg, 2 mg, 2.5 mg, 3 mg, 3.5 mg, 4 mg, 5 mg, 10 mg, 15 mg, 20 mg, 25 mg, 30 mg, 35 mg, 40 mg, 45 mg, 50 mg, 75 mg, 100 mg, 125 mg, 150 mg, 175 mg, 200 mg, 225 mg, 250 mg, 300 mg/kg of body weight of the patient.

In one example, the concentration of the administered compound is about 1 to about 100 mg/Kg of body weight of the patient, about 5 to about 100 mg/Kg of body weight of the patient, about 10 to about 100 mg/Kg of body weight of the patient, about 20 to about 100 mg/Kg of body weight of the patient, about 30 to about 100 mg/Kg of body weight of the patient, about 1 to about 50 mg/Kg of body weight of the patient, about 5 to about 50 mg/Kg of body weight of the patient and about 10 to about 50 mg/Kg of body weight of the patient.

As used herein, the term "about", in the context of amounts or concentrations of components of the formulations, typically means+/−5% of the stated value, more typically +/−4% of the stated value, more typically +/−3% of the stated value, more typically, +/−2% of the stated value, even more typically +/−1% of the stated value, and even more typically +/−0.5% of the stated value.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

Experimental Section

Methodology

Cell Culture

THP1 cells (human monocytic cell line) were maintained in Roswell Park Memorial Institute (RPMI1640) medium, supplemented with 10% fetal bovine serum (FBS), 1% Penicillin and 2 mM L-glutamine.

Preparation of Human Monocytes Derived Macrophages (hMDM)

Total blood was processed to isolate peripheral blood mononuclear cells (PBMCs) using ficoll gradient method. Monocytes were enriched from PBMCs using CD14 magnetic selection method (Miltenyi-Biotec beads). The purified CD14$^+$ monocytes were resuspended in RPMI1640 medium with 10% FBS, 1% Penicillin, 2 mM L-glutamine and 100 ng/ml human MCSF (R&D systems, USA) and incubated in 6 well plate at 37° C. in 5% $CO_2$ for seven days. The media was changed on 4th day. On Day 6 differentiated macrophages were collected after gentle wash, centrifuged, replated in fresh medium without human MCSF and cultured over night. On Day 7 cells were washed and used for different experiments.

Bacterial Strains and Growth Conditions

*Mycobacterium tuberculosis* H37Rv and *Mycobacterium bovis* BCG strains were grown in Middlebrook 7H9 broth (BBL Microbiology Systems, USA) supplemented with ADC (Difco laboratories, USA) and 0.05% Tween 80 at 37° C. for 5-7 days to an optical density of 0.5 ($OD_{600}$). After this mycobacterial cells were pelleted, resuspended in fresh 7H9 broth with 20% glycerol and stored at −80° C. On the day of infection the cells were thawed, washed, and sonicated before using them in experiments.

In Vitro BCG and MTB Infections

To prepare mycobacteria for infection, frozen vial of mycobacteria (BCG or MTB, with predetermined CFU) was thawed, washed by centrifugation, and pellet was resuspended in antibiotic free RPMI1640 with 10% FBS. This resuspended mycobacteria was used to infect THP1 cells and hMDM in 6 well plate with the multiplicity of infection (MOI) of 5. The infected cells were incubated at 37° C. with 5% $CO_2$ for 3 h. After that cells were washed two times with antibiotic free medium by centrifuging at 800 rpm. The infected cells were counted, seeded in triplicates and either left untreated or treated by different compounds dissolved in 0.1% DMSO. At respective time point's cells were utilized for various assays.

In Vitro Determination of Minimum Inhibitory Concentration

The minimum inhibitory concentration (MIC) of different compounds was determined using micro dilution method. The log phase culture of BCG (with $OD_{600}$=0.5) was adjusted to an $OD_{600}$ of 0.02 by 7H9-ADC. 200 µl of this was plated in a well of 96 well plate along with different concentration of various compounds. The BCG plate treated with various compounds was incubated at 37° C. with 5% $CO_2$ for 4 days after which $OD_{600}$ was measured. Experiment was conducted in triplicate.

Enumeration of Mycobacteria in Infected Cells

At pre-determined time point post-infection the infected cells were washed once with 1×PBS and then lysed with 200 µl of 1×PBS with 1% SDS. Various dilutions of this lysate were plated on Middlebrook 7H11 agar supplemented with 10% oleic acid-albumin-dextrose-catalase (OADC, Difco laboratories), in triplicates. Agar plates were incubated at 37° C. for 3 weeks after which colonies were counted visually. CFU (colony forming unit) obtained from two or three dilutions were used to calculate the total number of CFU/ml. Data is presented as percentage of mycobacteria survival in compounds treated cells versus untreated cells.

Measurement of ROS Production Upon Mycobacterial Infection

At pre-determined time points mycobacteria infected cells were harvested, washed with 1×HBSS and resuspended in either 1×HBSS with 10 M MitoSox™ or 1×HBSS with 5 µM of $CM-H_2DCFDA$ (both dyes from Molecular Probes, USA). Cells were incubated at 37° C. with 5% $CO_2$ for 15 minutes, washed with 1×HBSS and resuspended in 200 µl of 1×HBSS. The stained cells were than acquired using flowcytometer (BD Canto, Becton Dickinson, USA). Analysis was carried out using FlowJo software.

Measurement of BCG in Lysosomes

THP1 and hMDM cells were infected with AF488-labeled BCG. After infection cells were cultured in the presence of 25 µM of LysoTracker (LTR, Invitrogen) in the presence or absence of 2 mM of Metformin for either 4 or 16 h. Post-infection cells were washed with 1×PBS and fixed for 20 min at room temperature in 4% parformaldehyde. Fixed cells were washed with 1×PBS and mounted in FluorSave (Calbiochem). Fluorescent intensities of AF488-labeled BCG and LTR was analyzed using an Olympus FV1000 confocal microscope, which was then used to calculate the number of bacteria colocalized with LTR out of total number of bacteria counted. In total 50-60 infected cells were counted for different analysis.

In Vivo MTB Infections

The in vivo anti-tubercular activity of Metformin and resveratrol was evaluated in acute infection model of C57BL/6 mice. In total 5 experiments were performed. Six-eight weeks old female mice were infected using nose only aerosolization system (CH Technologies, USA). Animals were sacrificed at Day 1 to determine the number of bacteria implanted in the lungs. Seven days after post-infection animals were randomly grouped into different groups followed by the start of treatment. Mice were sacrificed at pre-determined time points followed by harvesting of tissues for MTB enumeration.

Enumeration of MTB in Infected Mouse

The mycobacteria load in the lung and spleen of infected mice was quantified by plating tissue homogenates on Middlebrook 7H11 agar supplemented with OADC. Briefly, at pre-determined time point post-infection/post-treatment mice were euthanized. Lungs and spleen were aseptically excised, washed in PBS and homogenized using 1×PBS with 0.25% Tween 80 and MACS tissue dissociater (Miltenyi Biotech, USA). Various dilutions of tissue homogenates were plated on Middlebrook 7H11 agar plates in triplicates. Agar plates were incubated at 37° C. for 3 weeks after which colonies were counted visually. CFU obtained from two or three dilutions were used to calculate the total number of CFU/tissue/mouse.

Statistical Analysis

Data were analyzed with parametric and non-parametric t-test or Chi-square test using GrapPad Prism 5 (GraphPad software). P-values of less than 0.05 were considered statistically significant.

Example 1

Identification of Intracellular Mycobacterial Growth Inhibitors

THP1 cells (human monocytic cell line) infected with *Mycobacterium bovis* (BCG) were treated for 24 hrs with 1, 10 or 100 µM of the following drugs (dissolved in 0.1% DMSO):
1. Bay K8644
2. R-(+)-Bay K8644
3. S-(+)-Bay K8644
4. FPL 64176
5. 2' 5'-Dideoxyadenosine (2'5'-ddA)
6. Rilmenidine
7. Loperamide
8. Nimodipine
9. Nitrendipine
0.10. KT 5720
11. Rapamycin (as a positive control)
12. Verapamil
13. Amiodarone
14. Metformin
15. Resveratrol
16. AICAR.

Figure 2:
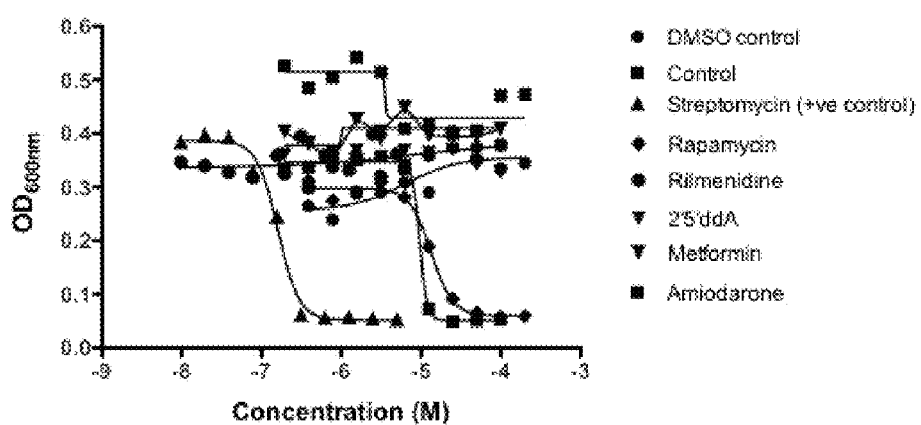
FIG. 2 shows line curve of Minimum Inhibitory Concentration (MIC) assay result of various compounds on the in vitro BCG growth. MIC was determined by the broth microdilution method after 5 days of incubation of BCG with different compounds at 37° C. In this experiment streptomycin, a known anti-TB drug, was used as a positive control and its $IC_{50}$ was approximately 0.2 µM. Representative of three independent experiments. Values are expressed as mean±SEM.
Figure 2:
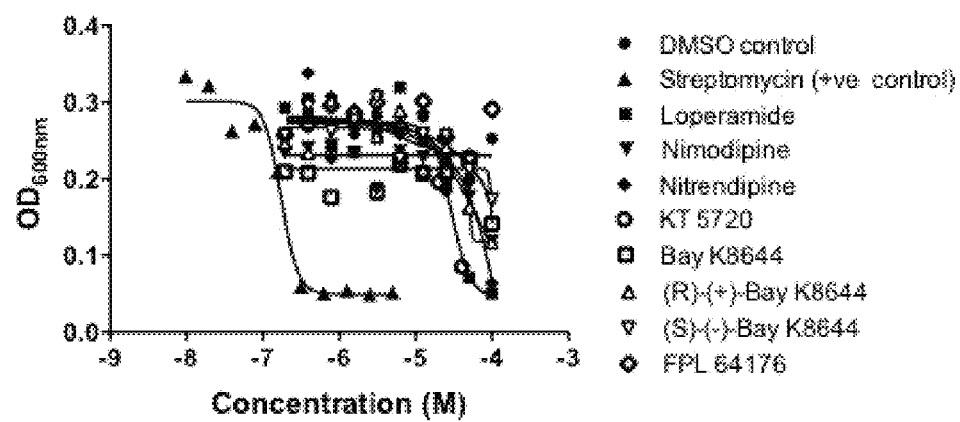

Following drug treatment, THP1 cells were lysed and mycobacterial viability was determined by counting bacteria colony forming units (CFU). The following agents significantly inhibited intracellular mycobacterial growth (FIG. 1).
1. Bay K8644
2. S-(+)-Bay K8644
3. FPL 64176
4. 2'-5'-Dideoxyadenosine
5. Loperamide
6. KT 5720
7. Metformin
8. Rilmenidine
9. Resveratrol When these compounds were tested for direct anti-mycobacterial activity in the standard Minimal Inhibitory Concentration (MIC) assay only rapamycin and amiodarone showed inhibition of mycobacterial growth (FIG. 2A), suggesting that these compounds can directly target mycobacterial machinery. The $IC_{50}$ of rapamycin and amiodarone were approx 13.8 and 9.6 µM respectively. However none of the compounds that inhibited growth of intracellular mycobacteria (FIG. 1) exhibited a direct anti-mycobacterial activity (FIG. 2).

Example 2

Metformin Induces Dose-Dependent Inhibition of Intra-Cellular Mycobacterial Growth Metformin, a drug belonging to biguanide group and a known AMPK activator, was selected from the compounds that showed activity against intracellular mycobacteria for further evaluation. This drug is commonly prescribed for the treatment of type 2 diabetes and has a proven safety record with a maximum dose of 2550 mg/day in humans.

Figure 3:
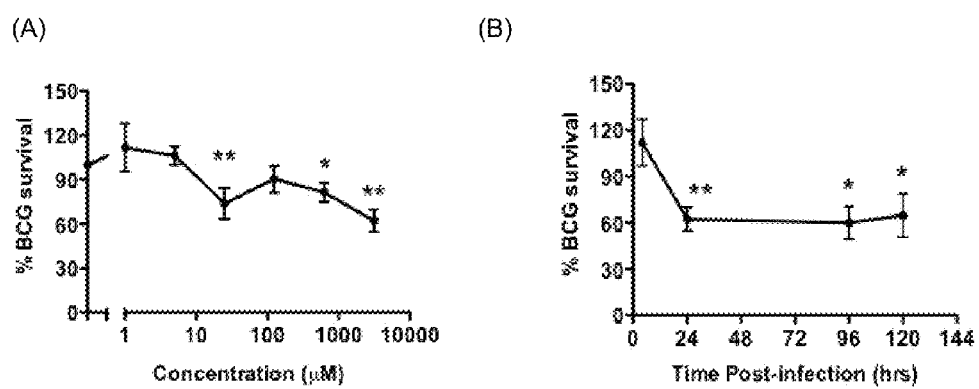
FIG. 3 shows line curve demonstrating the inhibition of intracellular mycobacteria. THP1 cells were infected with BCG (MOI of 5) for 3 hrs. Infected cells were washed and were either left untreated or treated with Metformin. After the indicated time points cells were lysed and mycobacterial viability (CFU) was determined (expressed as relative to untreated controls). (A) Shows results of inhibition of BCG growth by different concentrations of Metformin and CFU determined at 24 hrs; (B) Shows BCG survival as investigated at different time points after the addition of 2 mM Metformin. Values are expressed as mean±SEM. *, $p<0.05$; **, $p<0.01$, Student's t-test. Thus, FIG. 3 demonstrates that Metformin inhibits growth of intracellular mycobacteria in dose-dependent manner. That is, the higher the concentration of Metformin used, the more inhibition of intracellular mycobacteria was observed.

In the cellular assays as described herein, Metformin showed dose-dependent inhibition of intracellular mycobacteria (FIG. 3A). The inhibition of mycobacterial growth induced by Metformin occurred within the initial 24 hrs and no further reduction of mycobacterial survival was observed at later time points (FIG. 3B). No cellular toxicity was detectable up to 72 hrs after Metformin addition, when a dose of 2 mM was tested.

Example 3

Figure 4:
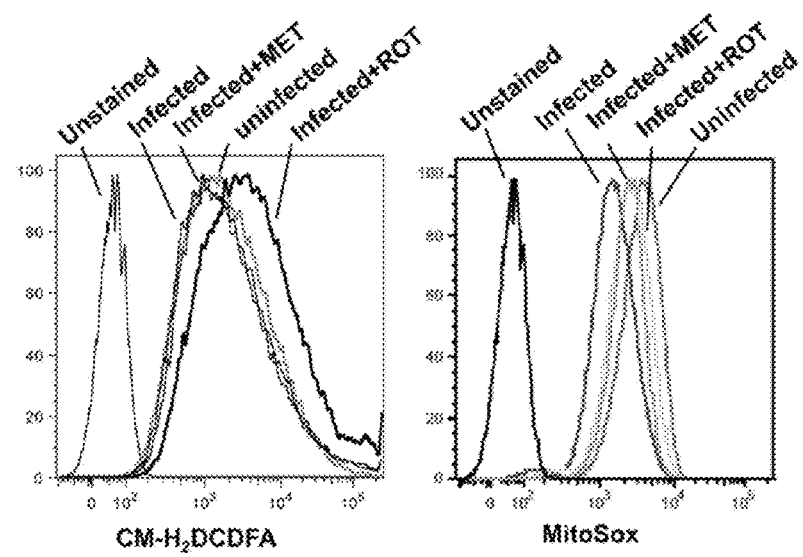
FIG. 4 shows results of investigation of the antimicrobial mechanism of Metformin against intracellular mycobacteria. THP1 cells were infected with BCG (MOI of 5) for 3 hrs. Infected cells were washed and treated with 2 mM Metformin or 1 µM rotenone for 4 hrs. Cells were harvested and stained with MitoSox™ and CM-H₂DCFDA (a chloromethyl derivative of H₂DCFDA) for identification of mitochondrial reactive oxygen species (mROS) and cytoplasmic reactive oxygen species (cROS) respectively by flow cytometry. (A) Shows representative histograms depicting fluorescence intensity of CM-H2DCDFA and MitoSox™, and their respective median fluorescent intensity (MFI) values. (B) Shows reactive oxygen species (ROS) production in treated or untreated infected cells presented as fold change of the MFI of MitoSox™ or CM-H2DCFDA relative to untreated infected cells (control). Data is the composition of 4-6 independent experiments. Values are expressed as mean±SEM. Untreated-infected and untreated cells, MET-infected cells treated with Metformin, ROT-infected cells treated with rotenone. Thus.
Figure 4:
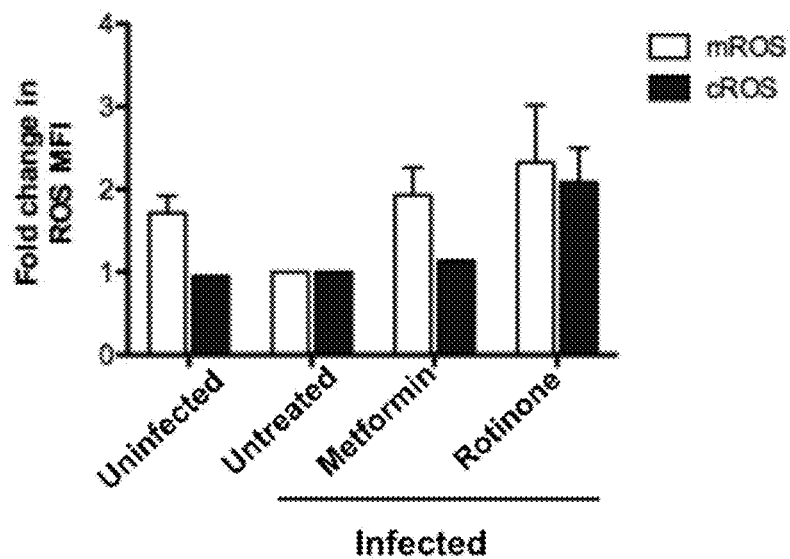

Metformin Prevents Intracellular Mycobacterial Growth by Increasing Mitochondrial Reactive Oxygen Species (mROS) Production Production of reactive oxygen species (ROS) is an innate immune response of host cells. Mycobacteria resist various bactericidal molecules produced by host cells including ROS, reactive nitrogen species (RNS), hydrolytic enzymes and acidic pH. To investigate the antimicrobial mechanism of Metformin against intracellular mycobacteria, ROS production was assessed in mycobacteria-infected THP1 cells. The addition of Metformin increased the production of mitochondrial ROS (mROS) but not of cytoplasmic ROS (cROS) in the infected cells at an early time point (4 hrs post-infection), as assessed by staining with the specific dyes, MitoSox™ and CM-$H_2$DCFDA, respectively (FIGS. 4A and 4B). Moreover it was observed that mycobacteria specifically suppress mROS production in infected macrophages (FIG. 4A, MFI of uninfected vs infected). As control, rotenone, known to produce ROS by inhibiting complex I, was added to the infected cells, which upregulated both mROS and cROS (FIG. 4).

Figure 5:
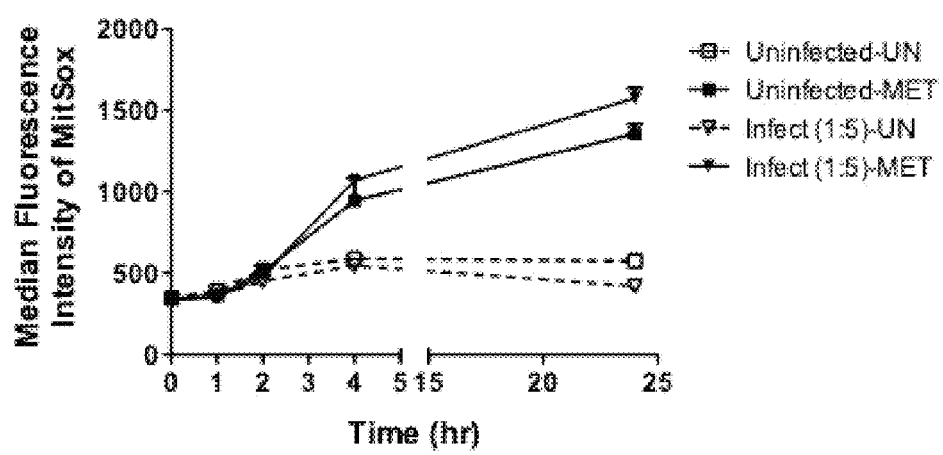
FIG. 5 shows line curve of mitochondrial reactive oxygen species produced over time and dose in cells treated with Metformin. (A) Shows THP1 cells infected with BCG (MOI of 5) for 3 hrs. Infected and uninfected cells were treated with 2 mM Metformin. Cells were harvested at indicated time points and stained with MitoSox™ for identification of mROS generation by flow cytometry. (B) Shows BCG infected THP1 cells treated with different concentrations of Metformin for 24 hrs, after which cells were harvested and stained with MitoSox™. Thus, FIG. 5 demonstrates the time and dose dependent nature of induction of mitochondrial reactive oxygen species (mROS) in infected cells upon Metformin treatment.
Figure 5:
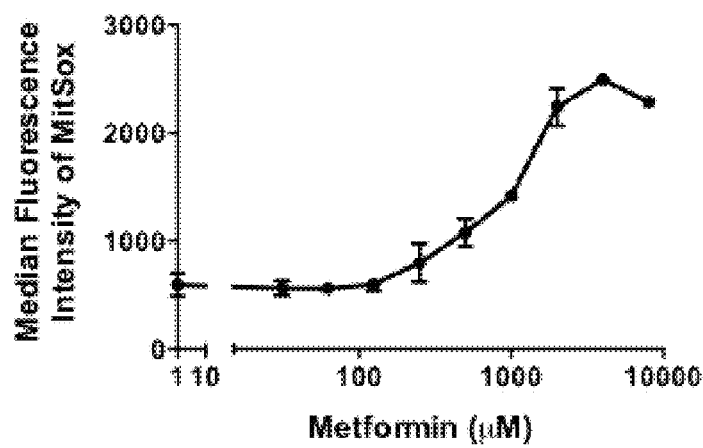

Furthermore it was observed that mROS increased significantly ($p<0.05$) in a time- and dose-dependent manner in cells treated with Metformin (FIGS. 5A and B), suggesting that Metformin inhibits BCG growth by facilitating mROS generation.

Figure 6:
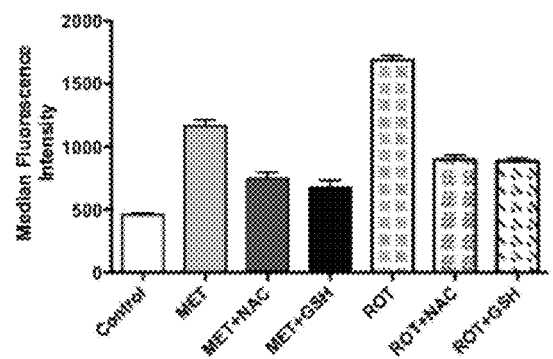
FIG. 6 shows bar graphs of mitochondrial reactive oxygen species (mROS) production and mycobacterial viability in infected cells upon Metformin treatment. THP1 cells or human monocyte-derived macrophages (hMDM) were infected with BCG (MOI of 5) for 3 hrs. Infected cells were washed and treated with 2 mM Metformin (MET) or 1 M rotenone (ROT) in the absence or presence of 10 mM of reactive oxygen species inhibitors, N-acetylcysteine (NAC) or glutathione (GSH) for 24 hrs. (A) Shows bar graph depicting MFI of mROS detected using MitoSox™; (B) Shows bar graph depicting percentage of BCG survival in THP1 cells; (C) Shows bar graph depicting percentage of BCG survival in hMDM. Values are Mean±SD. ***, $p<0.001$, Student's t-test. In these experiments difference between control (untreated infected cells) and MET+NAC/MET+GSH/NAC/GSH is not significant. Thus.
Figure 6:
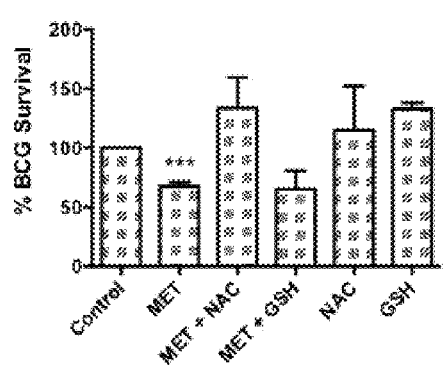
Figure 6:
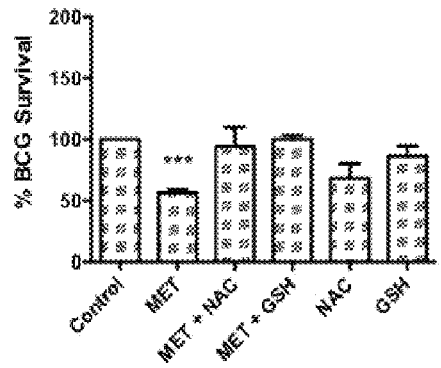

When production of mROS in infected THP1 cells upon Metformin treatment was inhibited using ROS scavengers such as N-acetylcysteine (NAC) and Glutathione (GSH) (FIG. 6A), an abolishment of Metformin-induced inhibition of growth of intracellular BCG (FIG. 6B) was observed. Similar results were obtained in primary human monocyte-derived macrophages (hMDM) infected with BCG (FIG. 6C). Altogether these findings suggested that the increased mROS generation induced by Metformin treatment is responsible for the inhibition of intracellular mycobacterial growth.

Example 4

Figure 7:
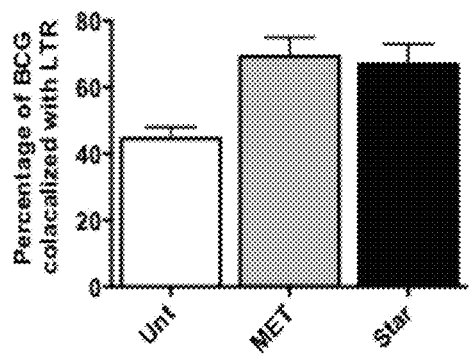
FIG. 7 shows bar graph of assay investigating fusion of phagosome with lysosome (i.e. acidity of mycobacterial phagosome) upon Metformin treatment of infected macrophages. Human monocyte-derived macrophages (hMDM) were infected with Alexa 488-labeled BCG (MOI of 5) for 3 hrs. Infected cells were washed and treated with 2 mM Metformin in the presence of 25 µM LysoTracker™ (LTR) for 12-16 hrs. After that cells were fixed, mounted with fluorsave and scanned by confocal microscope. Fifty-hundred infected cells were counted for each condition. Starved infected cells were used as positive control. Results are from two independent experiments and are expressed as percentage (%) of BCG co-localized with LTR. Unt—untreated infected cells, MET—Metformin treated infected cells, Star—starved infected cells. p=0.021, Chi-square test. Thus, FIG. 7 demonstrates Metformin induces acidification of mycobacteria-containing phagosomes.

Production of mROS by Metformin Induces Acidification of Mycobacterial Phagosomes Mycobacteria inhibit phagosome-lysososme fusion and thus prevent phagosome acidification, which leads to their intracellular survival. To investigate whether Metformin also restores phagosomal low pH, BCG infected cells were treated with Metformin in the presence of LysoTracker (LTR), a fluorescent probe that localizes in low pH cellular compartments i.e. lysosomes. Metformin induced 22% increase of mycobacteria localization in acidic compartments of infected hMDM compared to untreated cells (FIG. 7). In this experiment starved infected cells were kept as a positive control as starvation has been shown to acidify the mycobacterial phagosomes.

Figure 8:
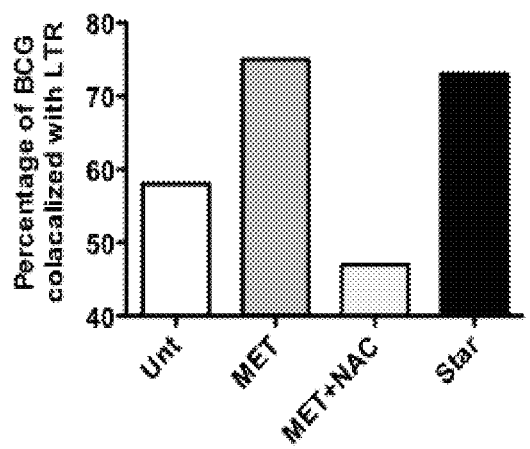
FIG. 8 shows bar graph of assay investigating fusion of mycobacterial phagosome with lysosome in the presence of NAC. hMDM were infected with Alexa 488-labeled BCG (MOI of 5) for 3 hrs. Infected cells were washed and treated with 2 mM MET and/or 10 mM NAC in the presence of 25 µM LysoTracker™ (LTR) for 4 hr. After that cells were fixed, mounted with fluorsave and scanned by confocal microscope. Fifty-hundred infected cells were counted for each condition. Starved infected cells were used as positive control. Results are expressed as percentage (%) of BCG colocalized with LTR. Unt—untreated infected cells, MET—Metformin treated infected cells, MET+NAC—Metformin and N-acetylcysteine treated infected cells, Star—starved infected cells. p=0.0065, Chi-square test. Thus, FIG. 8 demonstrates that scavenging ROS abolishes Metformin-induced acidification of mycobacteria-containing phagosomes.

It was further observed that quenching of ROS by NAC prevented Metformin-induced phagosomal acidification in BCG-infected macrophages (FIG. 8). Altogether these findings suggested that the upregulation of mROS induced by Metformin is instrumental to mycobacteria localization in acidic compartments and necessary to inhibit mycobacterial growth.

Example 5

Figure 9:
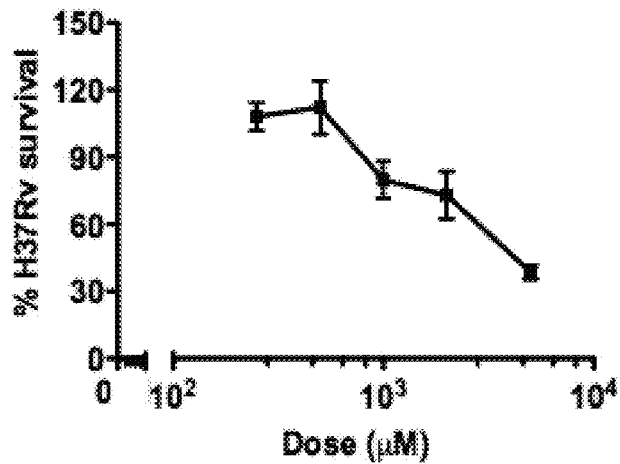
FIG. 9 shows a line curve of *Mycobacterium tuberculosis* (MTB) survival following Metformin treatment. THP1 cells were infected with H37Rv strain of *Mycobacterium tuberculosis* (MTB) (MOI of 5) for 3 hrs. Infected cells were washed and were either left untreated or treated with different concentrations of Metformin. After 24 hrs cells were lysed and mycobacterial viability (expressed as relative to untreated controls) was determined using CFU assay. The result is expressed as percentage of H37Rv survival. Thus.

Metformin Inhibits Intracellular Growth of *Mycobacterium tuberculosis* (MTB) by Producing Mitochondrial ROS Having observed the efficacy of Metformin against intracellular BCG (vaccine strain of *mycobacterium*, Example 1 and 2) additional cellular assays were performed to analyze the efficacy of Metformin against virulent *Mycobacterium tuberculosis* (MTB). In these experiments, Metformin showed dose-dependent inhibition of intracellular MTB (FIG. 9).

Figure 10:
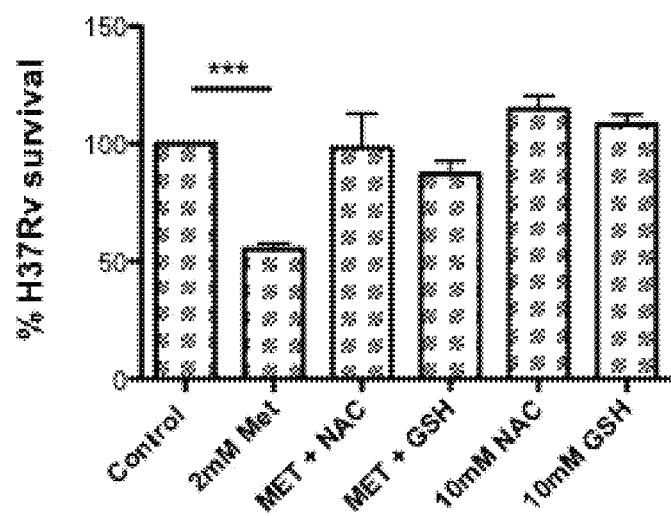
FIG. 10 shows bar graph of *Mycobacterium tuberculosis* (MTB) survival following Metformin treatment when combined with ROS inhibitors. THP1 cells were infected with H37Rv strain of *Mycobacterium tuberculosis* (MTB) (MOI of 5) for 3 hrs. Infected cells were washed and treated with 2 mM Metformin (MET) in the absence or presence of 10 mM of ROS inhibitors (NAC or GSH). After 24 hrs cells were lysed and mycobacterial viability (CFU) was determined. Values are Mean±SD. NAC-N-acetylcysteine; GSH-glutathione. ***, p<0.001. In these assays difference between control and MET+NAC/MET+GSH/NAC/GSH was not significant. Thus.

Metformin induces the production of mitochondrial reactive oxygen species (mROS), scavenging which abolishes Metformin-mediated inhibition of BCG growth (Example 3 and 4). Therefore we assessed the effect of Metformin on *Mycobacterium tuberculosis* (MTB) in infected THP1 cells in the presence of ROS inhibitors. In these experiments ROS inhibitors abolish the Metformin-mediated inhibition of intracellular *Mycobacterium tuberculosis* growth (FIG. 10). Altogether these findings suggest that the increased mROS generation induced by Metformin treatment is responsible for the inhibition of intracellular *Mycobacterium tuberculosis* (MTB).

Example 6

Metformin Inhibits *Mycobacterium tuberculosis* Growth in the Lungs of Mice and Enhances the Efficacy of Standard Tuberculosis Drugs An acute mouse model of tuberculosis chemotherapy was used to assess the mycobactericidal activity of Metformin either alone or in combination with standard tuberculosis drug i.e isoniazid (first line tuberculosis drug) and ethionamide (second line tuberculosis drug given to TB patients who have TB strain resistant to first line TB drugs). In this mouse model, depending on type of mouse strain used, reduction of 0.4-1 log 10 CFU in the tissues of drug treated mice compared to untreated, have been shown to have important biological significance. In the present invention Metformin is being investigated as an adjunctive host-directed therapy, hence similar reductions can have great clinical relevance.

C57BL/6 mice were infected by aerosol, achieving a mean day 1 lung implantation of ~2-3 $\log_{10}$ CFUs in different experiments. Drug treatment of *Mycobacterium tuberculosis* (MTB) infected mice was started after 7 days post-infection, the time at which the *Mycobacterium tuberculosis* (MTB) get establish in lung and the mean bacterial burden is ~4-5 $\log_{10}$ CFUs. In total 5 separate mouse experiments have been performed.

Figure 11:
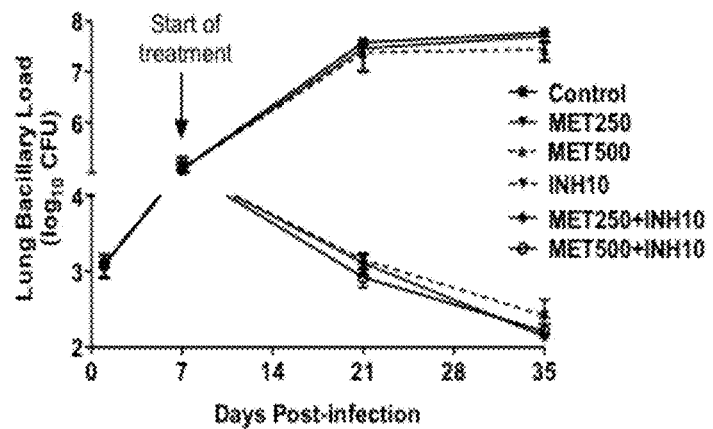
FIG. 11 shows results of two experiments on Metformin inhibition of *Mycobacterium tuberculosis* in mice. *Mycobacterium tuberculosis* (MTB) infected C57BL/6 mice were treated with 250 mg/Kg Metformin (MET250), 500 mg/Kg Metformin (MET500), 10 mg/Kg isoniazid (INH10, a first line tuberculosis drug), 10 mg/Kg isoniazid along with 250 mg/Kg Metformin (MET250+INH10) and 10 ing/Kg isoniazid along with 500 mg/Kg Metformin (MET500+INH10) from day 7 post-infection onwards. Drugs were resuspended in 0.5% of carboxy-methyl-cellulose (CMC). Treatment was performed orally and was given 6 days a week. Mice were sacrificed after 2 weeks and 4 weeks of treatment i.e. at day 21 and 35 post-infection. Controls—CMC treated mice. (A) Shows the profile of lung bacillary load in the mice during the course of experiment 1. (B) Shows lung bacillary load in the mice at day 35 post-infection in experiment 1. (C) Shows lung bacillary load in the mice at day 35 post-infection in experiment 2. Error bars represent SDs. N=5-7. Thus, FIG. 11 demonstrates that Metformin is capable of inhibiting growth of *Mycobacterium tuberculosis* in the lungs of mice.
Figure 11:
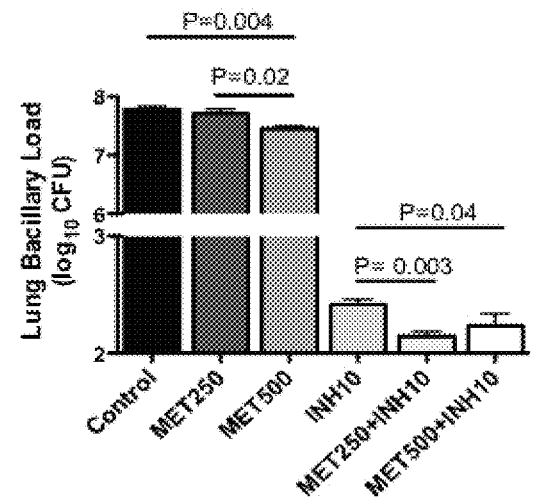
Figure 11:
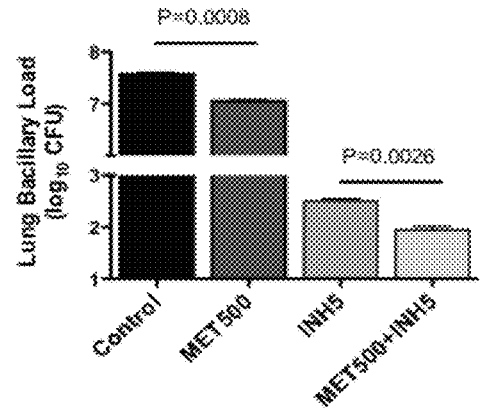

In the first experiment, *Mycobacterium tuberculosis* (MTB) infected mice were treated with 250 mg/Kg and 500 mg/Kg of Metformin (MET) either alone or in combination with 10 mg/Kg isoniazid (INH). Mice treated with 250 mg/Kg of Metformin had significantly less bacillary load at day 35 post-infection but not at day 21 post-infection (FIG. 11A). However, mice treated with 500 mg/Kg of Metformin had significantly less bacillary load both at day 21 and 35 post-infection (FIGS. 11A and B). In another experiment *Mycobacterium tuberculosis* (MTB) infected mice treated with 500 mg/Kg of Metformin had less lung CFU than control mice (FIG. 11c). Thus Metformin alone can decrease bacillary load in lungs. Mouse dose of 500 mg/Kg/day is approximately equivalent to human dose of 2430 mg/day.

Figure 12:
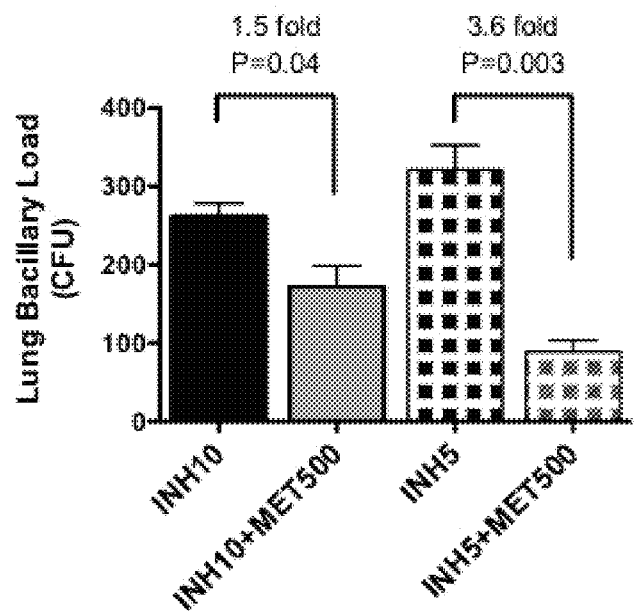
FIG. 12 shows a bar graph depicting lung bacillary load in *Mycobacterium tuberculosis* (MTB) infected mice treated with isoniazid, a first line tuberculosis drug, along with Metformin. *Mycobacterium tuberculosis* (MTB) infected C57BL/6 mice were treated with 5 or 10 mg/Kg isoniazid (INH5 and INH10, respectively) alone or in combination with 500 mg/Kg Metformin from day 7 post-infection onwards. Drugs were resuspended in 0.5% of carboxy-methyl-cellulose (CMC). Treatment was performed orally and was given 6 days a week. Mice were sacrificed after 4 weeks of treatment i.e. at day 35 post-infection. Controls—CMC treated mice. Fold difference in CFU between the group of mice treated with INH and Metformin compared to INH alone has been indicated. Error bars represent SDs. N=7-10. Thus.

In different experiments, when *Mycobacterium tuberculosis* (MTB) infected mice were treated with Metformin in conjunction with 5 or 10 mg/Kg of INH a 1.5 and 3.6 fold decrease in CFU, respectively with respect to INH alone was observed (FIG. 12). This indicates that Metformin can also enhance the efficacy of INH in clearing MTB from the lungs of mice.

Figure 13:
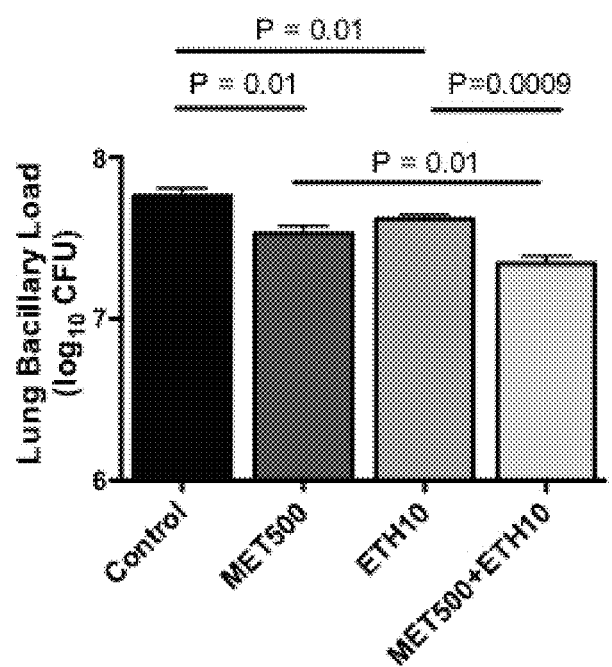
FIG. 13 shows a bar graph depicting inhibition of *Mycobacterium tuberculosis* in the lungs of mice with ethionamide, a known bacteriostatic tuberculosis drug, with or without Metformin. *Mycobacterium tuberculosis* (MTB) infected C57BL/6 mice were treated with 500 mg/Kg Metformin (MET500), 10 mg/Kg ethionamide (ETH10), and 10 mg/Kg ethionamide along with 500 mg/Kg Metformin (MET500+ETH10) from day 7 post-infection onwards. Drugs were resuspended in 0.5% CMC. Treatment was performed orally and was given 6 days a week. Mice were sacrificed after 4 weeks of treatment i.e. at day 35 post-infection. Controls—CMC treated mice. Error bars represent SDs. N=4-6.

In a separate experiment, *Mycobacterium tuberculosis* (MTB) infected mice were treated with ethionamide (ETH) in the presence and absence of Metformin. Ethionamide is known to be bacteriostatic and have little effect on mycobacterial numbers in the tissue. Like previous experiment (FIG. 11) Metformin alone decreased the bacillary load in the lungs and reduction in CFU is equivalent to that observed with 10 mg/Kg of ETH (ETH10, FIG. 13). When Metformin was administered in conjunction with ETH an enhanced *Mycobacterium tuberculosis* (MTB) clearance was observed compared to ETH alone or MET alone, indicating the additive effect of MET on the efficacy of ETH.

Example 7

Metformin Inhibits Dissemination of *Mycobacterium tuberculosis* to the Spleen of Mice The usual site of tuberculosis (TB) is the lungs, but other organs can be involved, where tuberculosis bacteria gets disseminated from the lung. Disseminated tuberculosis develops in the small number of infected people whose immune systems do not successfully contain the primary infection(s), such as people with AIDS. Disseminated disease can occur within weeks of the primary infection.

Figure 14:
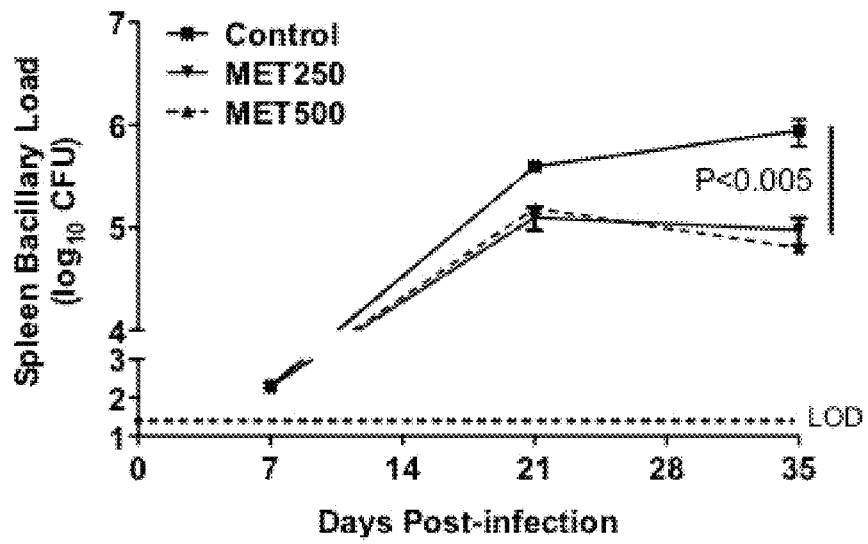
FIG. 14 shows spleen bacillary load in the *Mycobacterium tuberculosis* (MTB) infected mice treated with Metformin. *Mycobacterium tuberculosis* (MTB) infected C57BL/6 mice were treated with 250 mg/Kg Metformin (MET250), or 500 mg/Kg Metformin (MET500) from day 7 post-infection onwards. Drugs were resuspended in 0.5% of CMC. Treatment was performed orally and was given 6 days a week. Mice were sacrificed after 2 and 4 weeks of treatment i.e. at day 21 and 35 post-infection. Controls—CMC treated mice. Error bars represent SEM. LOD—limit of detection. N=4-7. Thus.

The mouse model was used to assess the effect of Metformin on the dissemination of *Mycobacterium tuberculosis* to spleen from lung. In the experiment described in FIG. 11, Metformin treated mice had significantly less *Mycobacterium tuberculosis* (MTB) CFU in the spleen compared to the control mice (FIG. 14).

Figure 15:
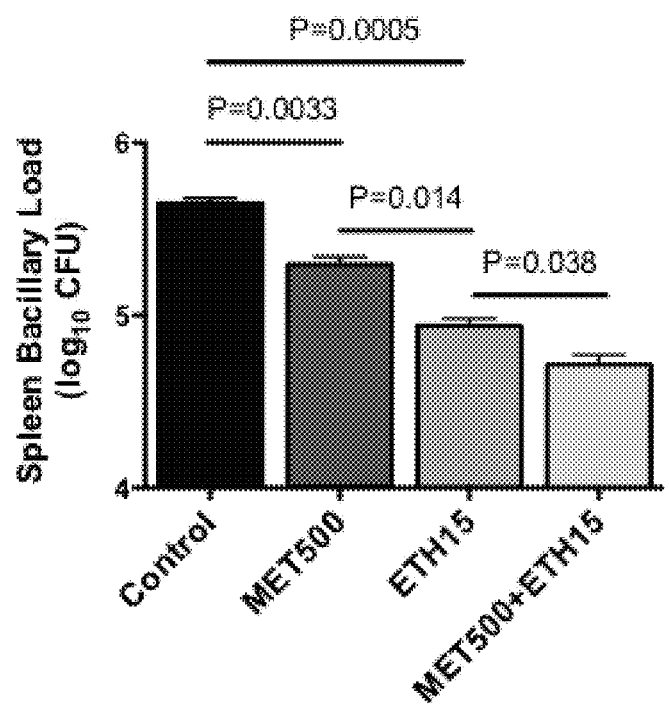
FIG. 15 shows assessment of the effect of Metformin on *Mycobacterium tuberculosis* (MTB) growth in the spleen of mice treated with ethionamide. *Mycobacterium tuberculosis* (MTB) infected C57BL/6 mice were treated with 500 mg/Kg Metformin (MET500), 15 mg/Kg ethionamide (ETH15), and 15 mg/Kg ethionamide along with 500 mg/Kg Metformin (MET500+ETH15) from day 7 post-infection onwards. Drugs were resuspended in 0.5% CMC. Treatment was performed orally and was given 6 days a week. Mice were sacrificed after 4 weeks of treatment i.e. at day 35 post-infection. Controls—CMC treated mice. Error bars represent SEM. N=4-6.

In a separate experiment *Mycobacterium tuberculosis* (MTB) infected mice were treated with 500 mg/Kg of Metformin and 15 mg/Kg of ethionamide followed by estimation of spleen CFU at day 35 post-infection. Mice treated with Metformin and ethionamide had significantly less bacteria in the spleen compared to the mice treated with ethionamide alone (FIG. 15), indicating again the adjunctive nature of Metformin.

Example 8

Resveratrol Inhibits *Mycobacterium tuberculosis* Growth in Mice and Enhances the Efficacy of Isoniazid The present disclosure has earlier shown the activity of Resveratrol (RES) on the growth of intracellular BCG in in vitro experiment (refer to FIG. 1C). Therefore, activity of RES against *Mycobacterium tuberculosis* was assessed in a mouse model. C57BL/6 mice were infected by aerosol, achieving a mean day 1 lung implantation of ~2-3 log 10 CFUs. Drug treatment of *Mycobacterium tuberculosis* (MTB) infected mice was started after 7 days post-infection.

Figure 16:
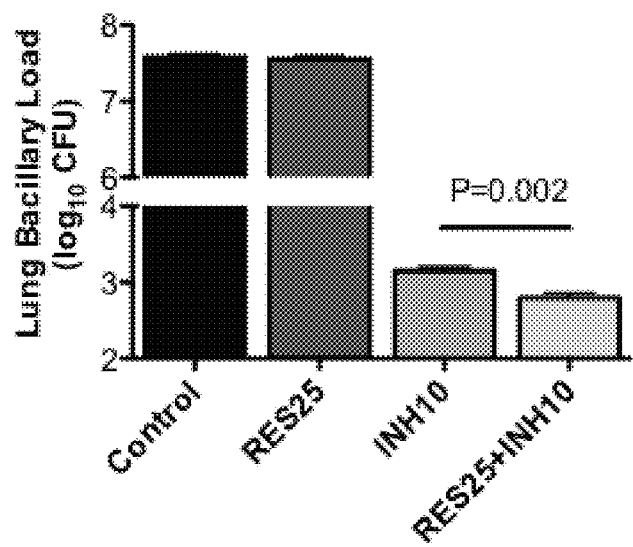
FIG. 16 shows the investigation into the activity of resveratrol against *Mycobacterium tuberculosis* in mice. *Mycobacterium tuberculosis* (MTB) infected C57BL/6 mice were treated with 25 mg/Kg resveratrol (RES25), 10 mg/Kg isoniazid (INH10), and 10 mg/Kg isoniazid along with 25 mg/Kg RES (RES25+INH10) from day 7 post-infection onwards. Drugs were resuspended in 0.5% CMC. Treatment was performed orally and was given 6 days a week. Mice were sacrificed after 2 and 4 weeks of treatment i.e. at day 21 and 35 post-infection. (A) Shows lung bacillary load in the mice at day 21 post-infection, (B) Shows lung bacillary load in the mice at day 35 post-infection. Controls—CMC treated mice. Error bars represent SEM. N=6-8. Thus, FIG. 16 demonstrates capability of resveratrol to enhance the efficacy of isoniazid in controlling *Mycobacterium tuberculosis* (MTB) growth in the lungs.
Figure 16:
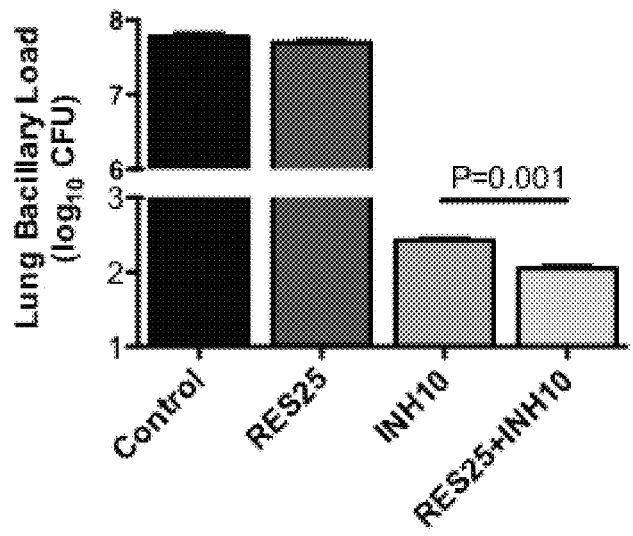
Figure 17:
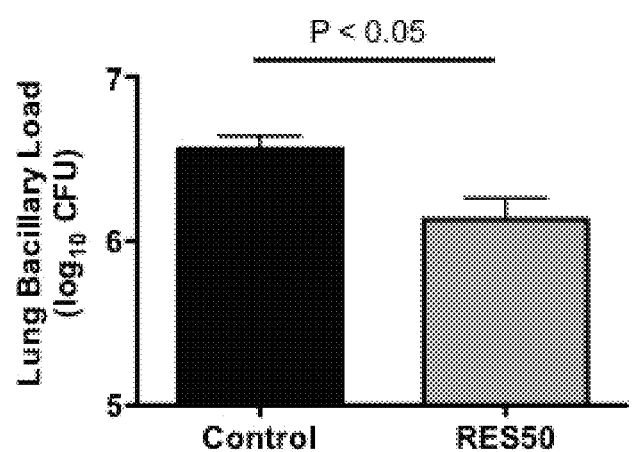
FIG. 17 shows the investigation into the activity of resveratrol against *Mycobacterium tuberculosis* in mice. *Mycobacterium tuberculosis* (MTB) infected C57BL/6 mice were treated with 50 mg/Kg resveratrol (RES50) from day 7 post-infection onwards. Drug was resuspended in 0.5% CMC. Treatment was performed orally and was given 6 days a week. Mice were sacrificed after 2 and 4 weeks of treatment i.e. at day 21 and 35 post-infection. Controls—CMC treated mice. (A) Lung bacillary load at day 35 post-infection, (B) Spleen bacillary load at day 21 post-infection. Error bars represent SEM. N=4-6. Thus, FIG. 17 demonstrates resveratrol to be capable of inhibiting growth of *Mycobacterium tuberculosis* (MTB) in the lungs and spleen of mice.
Figure 17:
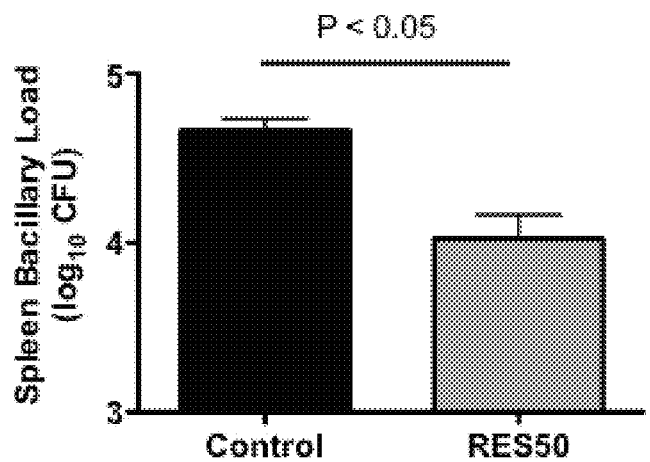

In the first experiment, *Mycobacterium tuberculosis* (MTB) infected mice were treated with 25 mg/Kg of RES either alone or in combination with 10 mg/Kg isoniazid (INH). In this experiment 25 mg/Kg dose of RES alone did not reduce the bacilli load in the lung compared to controls (FIG. 16). However when RES was administered in conjunction with INH (10 mg/Kg) an enhanced *Mycobacterium tuberculosis* (MTB) clearance was observed compared to INH alone both at day 21 and 35 post-infection (FIG. 16), indicating the additive effect of RES on the efficacy of INH. In this experiment as 25 mg/Kg dose of RES alone was not efficacious, another experiment was carried out where *Mycobacterium tuberculosis* (MTB) infected mice were treated with 50 mg/Kg of resveratrol (RES50). After 2-4 weeks of treatment (at 21 and 35 day post-infection) group of mice treated with RES50 had less CFU in the lung as well as spleen compared to control (FIG. 17), indicating the efficacy of RES against *Mycobacterium tuberculosis*. Oral $LD_{50}$ of RES for mice is ~2 g/Kg.

The invention claimed is:

1. A method of preventing, treating or inhibiting mycobacterial infections, the method comprising administering at least one of the compounds selected from the group consisting of:
    N,N-dimethyl imidodicarbonimidic diamide hydrochloride (Metformin);
    3,5,4'-trihydroxy-trans-stilbene (Resveratrol);
    methyl 2,6-dimethyl-5-nitro-4-[2-(trifluoromethyl)phenyl]-1,4-dihydropyridine-3-carboxylate (Bay K8644);
    2,5-Dimethyl-4-[2-(phenylmethyl)benzoyl]-1H-pyrrole-3-carboxylic acid methyl ester (FPL 64176);
    2',5'-Dideoxyadenosine;
    4-[4-(4-chlorophenyl)-4-hydroxypiperidin-1-yl]-N,N-dimethyl-2,2-diphenylbutanamide hydrochloride (Loperamide);
    (5R,6S,8S)-Hexyl 6-hydroxy-5-methyl-13-oxo-6,7,8,13,14,15-hexahydro-5H-16-oxa-4b,8a,14-triaza-5,8-methanodibenzo[b,h]cycloocta[jkl]cyclopenta[e]-as-indacene-6-carboxylate (KT 5720);
    N-(dicyclopropylmethyl)-4,5-dihydro-1,3-oxazol-2-amine (Rilmenidine);
    3-(2-methoxyethyl) 5-propan-2-yl 2,6-dimethyl-4-(3-nitrophenyl)-1,4-dihydropyridine-3,5-dicarboxylate (Nimodipine);
    (RS)-ethyl methyl 2,6-dimethyl-4-(3-nitrophenyl)-1,4-dihydropyridine-3,5-dicarboxylate (Nitrendipine);
    (2-{4-[(2-butyl-1-benzofuran-3-yl)carbonyl]-2,6-diiodophenoxy}ethyl)diethylamine (Amiodarone); and
    [(2R,3S,4R,5R)-5-(4-Carbamoyl-5-aminoimidazol-1-yl)-3,4-dihydroxyoxolan-2-yl]methyl dihydrogen phosphate (AICAR), to a patient in need thereof, wherein the method further comprises administration of an anti-tuberculosis drug, wherein the anti-tuberculosis drug is selected from the group consisting of isoniazid, pyrazinamide, rifampicin, ethionamide, rifabutin, amikacin, ethambutol, PA824, bedaquiline, streptomycin, kanamycin, and fluoroquinolone antibiotic or a combination thereof.

2. The method of claim 1, wherein the mycobacterial infection is an intracellular bacterial infection.

3. The method of claim 1, wherein the mycobacteria is selected from the group consisting of *M. tuberculosis, M. bovis, M. bovis BCG, M. africanum, M. canetti, M. caprae, M. microti, M. leprae, M. avium, M. paratuberculosis* and *M. pinnipedii*.

4. The method of claim 3, wherein the mycobacteria are *M. tuberculosis*.

5. The method of claim 3, wherein the mycobacteria are drug resistant *M. tuberculosis*.

6. The method of claim 1, wherein methyl 2,6-dimethyl-5-nitro-4-[2-(trifluoromethyl)phenyl]-1,4-dihydropyridine-3-carboxylate (Bay K8644) is S-(+)-methyl 2,6-dimethyl-5-nitro-4-[2-(trifluoromethyl)phenyl]-1,4-dihydropyridine-3-carboxylate (Bay K8644).

7. The method of claim 1, further comprising administering the anti-tuberculosis drug together or separately with any one of said compounds.

8. The method of claim 1, wherein the compounds are selected from the group consisting of N,N-dimethyl imidodicarbonimidic diamide hydrochloride (Metformin) and 3,5,4'-trihydroxy-trans-stilbene (Resveratrol).

9. The method of claim 1, wherein the concentration of the administered compound is about 1 to about 100 mg/Kg of body weight of the patient.

10. The method of claim 1, wherein the route of administration is selected from the group consisting of systemic administration, oral administration, intravenous administration and parenteral administration.

11. A method of increasing the acidity of bacterial phagosomes to inhibit mycobacterial growth in a cell, the method comprising contacting the cell with at least one of the compounds selected from the group consisting of:
    N,N-dimethyl imidodicarbonimidic diamide hydrochloride (Metformin);
    3,5,4'-trihydroxy-trans-stilbene (Resveratrol);
    methyl 2,6-dimethyl-5-nitro-4-[2-(trifluoromethyl)phenyl]-1,4-dihydropyridine-3-carboxylate (Bay K8644);
    2,5-Dimethyl-4-[2-(phenylmethyl)benzoyl]-1H-pyrrole-3-carboxylic acid methyl ester (FPL 64176);
    2',5'-Dideoxyadenosine;
    4-14-(4-chlorophenyl)-4-hydroxypiperidin-1-yl1-N,N-dimethyl-2,2-diphenylbutanamide hydrochloride (Loperamide);
    (5R,6S,8S)-Hexyl 6-hydroxy-5-methyl-13-oxo-6,7,8,13,14,15-hexahydro-5H-16-oxa-4b,8a,14-triaza-5,8-methanodibenzo[b,h]cycloocta[jkl]cyclopenta[e]-as-indacene-6-carboxylate (KT 5720);
    N-(dicyclopropylmethyl)-4,5-dihydro-1,3-oxazol-2-amine (Rilmenidine);
    3-(2-methoxyethyl) 5-propan-2-yl2,6-dimethyl-4-(3-nitrophenyl)-1,4-dihydropyridine-3,5-dicarboxylate (Nimodipine);
    (RS)-ethyl methyl 2,6-dimethyl-4-(3-nitrophenyl)-1,4-dihydropyridine-3,5-dicarboxylate (Nitrendipine);
    (2-{4-[(2-butyl-1-benzofuran-3-yl)carbonyl]-2,6-diiodophenoxy}ethyl)diethylamine (Amiodarone); and
    [(2R,3S,4R,5R)-5-(4-Carbamoyl-5-aminoimidazol-1-yl)-3,4-dihydroxyoxolan-2-yl]methyl dihydrogen phosphate (AICAR), wherein the method further comprises administration of an anti-tuberculosis drug, wherein the anti-tuberculosis drug is selected from the group consisting of isoniazid, pyrazinamide, rifampicin, ethionamide, rifabutin, amikacin, ethambutol, PA824, bedaquiline, streptomycin, kanamycin, and fluoroquinolone antibiotic or a combination thereof.

12. A method of increasing mitochondrial reactive oxygen species (mROS) generation to inhibit mycobacterial growth in a cell, the method comprising contacting the cell with at least one of the compounds selected from the group consisting of:

- N,N-dimethyl imidodicarbonimidic diamide hydrochloride (Metformin);
- 3,5,4'-trihydroxy-trans-stilbene (Resveratrol);
- methyl 2,6-dimethyl-5-nitro-4-[2-(trifluoromethyl)phenyl]-1,4-dihydropyridine-3-carboxylate (Bay K8644);
- 2,5-Dimethyl-4-[2-(phenylmethyl)benzoyl]-1H-pyrrole-3-carboxylic acid methyl ester (FPL 64176);
- 2',5'-Dideoxyadenosine;
- 4-14-(4-chlorophenyl)-4-hydroxypiperidin-1-yl1-N,N-dimethyl-2,2-diphenylbutanamide hydrochloride (Loperamide);
- (5R,6S,8S)-Hexyl 6-hydroxy-5-methyl-13-oxo-6,7,8,13,14,15-hexahydro-5H-16-oxa-4b,8a,14-triaza-5,8-methanodibenzo[b,h]cycloocta[jkl]cyclopenta[e]-as-indacene-6-carboxylate (KT 5720);
- N-(dicyclopropylmethyl)-4,5-dihydro-1,3-oxazol-2-amine (Rilmenidine);
- 3-(2-methoxyethyl) 5-propan-2-yl2,6-dimethyl-4-(3-nitrophenyl)-1,4-dihydropyridine-3,5-dicarboxylate (Nimodipine);
- (RS)-ethyl methyl 2,6-dimethyl-4-(3-nitrophenyl)-1,4-dihydropyridine-3,5-dicarboxylate (Nitrendipine);
- (2-{4-[(2-butyl-1-benzofuran-3-yl)carbonyl]-2,6-diiodophenoxy}ethyl)diethylamine (Amiodarone); and
- [(2R,3S,4R,5R)-5-(4-Carbamoyl-5-aminoimidazol-1-yl)-3,4-dihydroxyoxolan-2-yl]methyl dihydrogen phosphate (AICAR), wherein the method further comprises administration of an anti-tuberculosis drug, wherein the anti-tuberculosis drug is selected from the group consisting of isoniazid, pyrazinamide, rifampicin, ethionamide, rifabutin, amikacin, ethambutol, PA824, bedaquiline, streptomycin, kanamycin, and fluoroquinolone antibiotic or a combination thereof.

13. The method of claim 12, wherein the mycobacteria are drug resistant *M. tuberculosis*.

14. A pharmaceutical composition comprising:
at least one of the compounds selected from the group consisting of:
- N,N-dimethyl imidodicarbonimidic diamide hydrochloride (Metformin);
- methyl 2,6-dimethyl-5-nitro-4-[2-(trifluoromethyl)phenyl]-1,4-dihydropyridine-3-carboxylate (Bay K8644);
- 2,5-Dimethyl-4-[2-(phenylmethyl)benzoyl]-1H-pyrrole-3-carboxylic acid methyl ester (FPL 64176);
- 2',5'-Dideoxyadenosine;
- 4-[4-(4-chlorophenyl)-4-hydroxypiperidin-1-yl]-N,N-dimethyl-2,2-diphenylbutanamide hydrochloride (Loperamide);
- (5R,6S,8S)-Hexyl 6-hydroxy-5-methyl-13-oxo-6,7,8,13,14,15-hexahydro-5H-16-oxa-4b,8a,14-triaza-5,8-methanodibenzo[b,h]cycloocta[jkl]cyclopenta[e]-as-indacene-6-carboxylate (KT 5720);
- N-(dicyclopropylmethyl)-4,5-dihydro-1,3-oxazol-2-amine (Rilmenidine);
- 3-(2-methoxyethyl) 5-propan-2-yl 2,6-dimethyl-4-(3-nitrophenyl)-1,4-dihydropyridine-3,5-dicarboxylate (Nimodipine);
- (RS)-ethyl methyl 2,6-dimethyl-4-(3-nitrophenyl)-1,4-dihydropyridine-3,5-dicarboxylate (Nitrendipine);
- (2-{4-[(2-butyl-1-benzofuran-3-yl)carbonyl]-2,6-diiodophenoxy}ethyl)diethylamine (Amiodarone); and
- [(2R,3S,4R,5R)-5-(4-Carbamoyl-5-aminoimidazol-1-yl)-3,4-dihydroxyoxolan-2-yl]methyl dihydrogen phosphate (AICAR); and an anti-tuberculosis drug selected from the group consisting of isoniazid, pyrazinamide, rifampicin, ethionamide, rifabutin, amikacin, ethambutol, PA824, bedaquiline, streptomycin, kanamycin, and fluoroquinolone antibiotic or a combination thereof.

15. A method for eliciting an immune response to an intracellular mycobacteria, said method comprising administering at least one compound selected from the group consisting of:
- N,N-dimethyl imidodicarbonimidic diamide hydrochloride (Metformin);
- 3,5,4'-trihydroxy-trans-stilbene (Resveratrol);
- methyl 2,6-dimethyl-5-nitro-4-[2-(trifluoromethyl)phenyl]-1,4-dihydropyridine-3-carboxylate (Bay K8644);
- 2,5-Dimethyl-4-[2-(phenylmethyl)benzoyl]-1H-pyrrole-3-carboxylic acid methyl ester (FPL 64176);
- 2',5'-Dideoxyadenosine;
- 4-[4-(4-chlorophenyl)-4-hydroxypiperidin-1-yl]-N,N-dimethyl-2,2-diphenylbutanamide hydrochloride (Loperamide);
- (5R,6S,8S)-Hexyl 6-hydroxy-5-methyl-13-oxo-6,7,8,13,14,15-hexahydro-5H-16-oxa-4b,8a,14-triaza-5,8-methanodibenzo[b,h]cycloocta[jkl]cyclopenta[e]-as-indacene-6-carboxylate (KT 5720);
- N-(dicyclopropylmethyl)-4,5-dihydro-1,3-oxazol-2-amine (Rilmenidine);
- 3-(2-methoxyethyl) 5-propan-2-yl 2,6-dimethyl-4-(3-nitrophenyl)-1,4-dihydropyridine-3,5-dicarboxylate (Nimodipine);
- (RS)-ethyl methyl 2,6-dimethyl-4-(3-nitrophenyl)-1,4-dihydropyridine-3,5-dicarboxylate (Nitrendipine);
- (2-{4-[(2-butyl-1-benzofuran-3-yl)carbonyl]-2,6-diiodophenoxy}ethyl)diethylamine (Amiodarone); and
- [(2R,3S,4R,5R)-5-(4-Carbamoyl-5-aminoimidazol-1-yl)-3,4-dihydroxyoxolan-2-yl]methyl dihydrogen phosphate (AICAR), wherein the method further comprises administration of an antituberculosis drug, wherein the anti-tuberculosis drug is selected from the group consisting of isoniazid, pyrazinamide, rifampicin, ethionamide, rifabutin, amikacin, ethambutol, PA824, bedaquiline, streptomycin, kanamycin, and fluoroquinolone antibiotic or a combination thereof.

* * * * *

UNITED STATES PATENT AND TRADEMARK OFFICE
CERTIFICATE OF CORRECTION

PATENT NO. : 9,539,222 B2
APPLICATION NO. : 14/426659
DATED : January 10, 2017
INVENTOR(S) : Singhal et al.

Page 1 of 1

It is certified that error appears in the above-identified patent and that said Letters Patent is hereby corrected as shown below:

On the Title Page

In Column 2, under "Other Publications", Line 17, delete "$CA_{2+}$" and insert --$CA^{2+}$--, therefor In the Claims In Column 24, Line 41-43, in Claim 11, delete "4-14-(4-chlorophenyl)-4-hydroxypiperidin-1-yl1-N,N-dimethyl-2,2-diphenylbutanamide hydrochloride (Loperamide);" and insert --4-[4-(4-chlorophenyl)-4-hydroxypiperidin-1-yl]-N,N-dimethyl-2,2-diphenylbutanamide hydrochloride (Loperamide);--, therefor In Column 24, Line 50-52, in Claim 11, delete "3-(2-methoxyethyl) 5-propan-2-yl2,6-dimethyl-4-(3-nitrophenyl)-1,4-dihydropyridine-3,5-dicarboxylate (Nimodipine);" and insert --3-(2-methoxyethyl) 5-propan-2-yl 2,6-dimethyl-4-(3-nitrophenyl)-1,4-dihydropyridine-3,5-dicarboxylate (Nimodipine);--, therefor In Column 25, Line 12-14, in Claim 12, delete "4-14-(4-chlorophenyl)-4-hydroxypiperidin-1-yl1-N,N-dimethyl-2,2-diphenylbutanamide hydrochloride (Loperamide);" and insert --4-[4-(4-chlorophenyl)-4-hydroxypiperidin-1-yl]-N,N-dimethyl-2,2-diphenylbutanamide hydrochloride (Loperamide);--, therefor In Column 25, Line 21-23, in Claim 12, delete "3-(2-methoxyethyl) 5-propan-2-yl2,6-dimethyl-4-(3-nitrophenyl)-1,4-dihydropyridine-3,5-dicarboxylate (Nimodipine);" and insert --3-(2-methoxyethyl) 5-propan-2-yl 2,6-dimethyl-4-(3-nitrophenyl)-1,4-dihydropyridine-3,5-dicarboxylate (Nimodipine);--, therefor Signed and Sealed this
Third Day of April, 2018

Andrei Iancu
*Director of the United States Patent and Trademark Office*